(12) United States Patent
Li et al.

(10) Patent No.: US 7,622,523 B2
(45) Date of Patent: *Nov. 24, 2009

(54) PLASTICIZED POLYOLEFIN COMPOSITIONS

(75) Inventors: Wen Li, Houston, TX (US); Chon Y. Lin, Houston, TX (US); Bryan R. Chapman, Annandale, NJ (US); Bruce R. Lundmark, Waller, TX (US); David J. Lohse, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 145 days.

This patent is subject to a terminal disclaimer.

(21) Appl. No.: 11/054,247

(22) Filed: Feb. 9, 2005

(65) Prior Publication Data

US 2005/0148720 A1 Jul. 7, 2005

Related U.S. Application Data

(63) Continuation-in-part of application No. 10/640,435, filed on Aug. 12, 2003, and a continuation-in-part of application No. 10/634,351, filed on Aug. 4, 2003.

(60) Provisional application No. 60/544,108, filed on Feb. 12, 2004, provisional application No. 60/402,665, filed on Aug. 12, 2002.

(51) Int. Cl.
  *C08K 5/01* (2006.01)
  *C08L 23/12* (2006.01)
  *C08L 23/14* (2006.01)
  *C08J 3/18* (2006.01)

(52) U.S. Cl. .................. 524/491; 524/490; 524/848; 524/582; 524/583; 522/157; 522/80; 428/365; 604/187

(58) Field of Classification Search ............ 524/579, 524/582, 583, 584, 585, 586, 587, 575, 490, 524/491, 848; 525/240, 190
See application file for complete search history.

(56) References Cited

U.S. PATENT DOCUMENTS

| | | |
|---|---|---|
| 2,567,016 A | 9/1951 | Gessler et al. |
| 3,149,178 A | 9/1964 | Hamilton et al. |
| 3,201,364 A | 8/1965 | Salyer |
| 3,228,896 A | 1/1966 | Canterino |
| 3,235,529 A | 2/1966 | Nagle |
| 3,239,478 A | 3/1966 | Harlan, Jr. |
| 3,281,390 A | 10/1966 | O'Leary, Jr. |
| 3,299,568 A | 1/1967 | Tobolsky |
| 3,308,086 A | 3/1967 | Wartman |
| 3,318,835 A | 5/1967 | Hagemeyer, Jr. et al. |
| 3,338,778 A | 8/1967 | Hutchins et al. |
| 3,361,702 A | 1/1968 | Wartman et at. |
| 3,415,925 A | 12/1968 | Marans et al. |
| 3,437,627 A | 4/1969 | Gude et al. |
| 3,439,088 A | 4/1969 | Edman |
| 3,464,949 A | 9/1969 | Wartman et al. |
| 3,475,368 A | 10/1969 | Metz |
| 3,536,796 A | 10/1970 | Rock |
| 3,541,039 A | 11/1970 | Whiton |
| 3,563,934 A | 2/1971 | Burnett |
| 3,590,528 A | 7/1971 | Shepherd |
| 3,686,385 A | 8/1972 | Rohn |
| 3,752,779 A | 8/1973 | Maciejewski |
| 3,818,105 A | 6/1974 | Coopersmith et al. |
| 3,821,148 A | 6/1974 | Makowski et al. |
| 3,828,105 A | 8/1974 | Saurano et al. |
| 3,839,261 A | 10/1974 | Aronoff et al. |
| 3,860,543 A | 1/1975 | Masuda et al. |
| 3,894,120 A | 7/1975 | Frese et al. |
| 3,925,504 A | 12/1975 | Koleske et al. |
| 3,925,947 A | 12/1975 | Meyers et al. |
| 3,945,975 A | 3/1976 | Strack |
| 3,957,898 A | 5/1976 | Girotti et al. |
| 3,988,276 A | 10/1976 | Kutch et al. |
| 4,006,115 A | 2/1977 | Elbert |
| 4,010,127 A | 3/1977 | Taka et al. |
| 4,038,238 A | 7/1977 | Cravens |
| 4,041,002 A | 8/1977 | Aboshi et al. |
| 4,041,103 A | 8/1977 | Davison et al. |
| 4,061,805 A | 12/1977 | Thompson et al. |
| 4,063,002 A | 12/1977 | Wilson, Jr. |
| 4,073,782 A | 2/1978 | Kishi et al. |
| 4,087,505 A | 5/1978 | Sugimoto et al. |
| 4,092,282 A | 5/1978 | Callan |
| 4,094,850 A | 6/1978 | Morgan et al. |
| 4,097,543 A | 6/1978 | Haag et al. |
| 4,104,216 A | 8/1978 | Clampitt |
| 4,110,185 A | 8/1978 | Williams et al. |
| 4,113,802 A | 9/1978 | Matteoli et al. |
| 4,118,359 A | 10/1978 | Brenner |
| 4,118,362 A | 10/1978 | Makowski et al. |
| 4,131,587 A | 12/1978 | Brenner |
| 4,132,698 A | 1/1979 | Gessler et al. |
| 4,136,072 A | 1/1979 | Ladish et al. |
| 4,138,378 A | 2/1979 | Doss |
| 4,147,831 A | 4/1979 | Balinth |
| 4,153,582 A | 5/1979 | Puffr et al. |
| 4,153,588 A | 5/1979 | Makowski et al. |

(Continued)

FOREIGN PATENT DOCUMENTS

CS  215313  8/1982

(Continued)

OTHER PUBLICATIONS

JP 1-192365 (abstract and translation in English).*

(Continued)

*Primary Examiner*—David Wu
*Assistant Examiner*—Rip A. Lee
(74) *Attorney, Agent, or Firm*—Kevin M. Faulkner; Catherine L. Bell

(57) ABSTRACT

The present invention relates to radiation resistant plasticized polyolefin compositions comprising a polyolefin and a non-functionalized hydrocarbon plasticizer.

64 Claims, No Drawings

U.S. PATENT DOCUMENTS

| | | |
|---|---|---|
| 4,153,594 A | 5/1979 | Wilson, Jr. |
| 4,154,244 A * | 5/1979 | Becker et al. .......... 604/103.11 |
| 4,154,712 A | 5/1979 | Lee, Jr. |
| 4,157,992 A | 6/1979 | Lundberg et al. |
| 4,166,057 A | 8/1979 | Takemori |
| 4,169,822 A | 10/1979 | Kutch et al. |
| 4,170,586 A | 10/1979 | Clampitt et al. |
| 4,175,069 A | 11/1979 | Brenner |
| 4,189,411 A | 2/1980 | Haaf |
| 4,210,570 A | 7/1980 | Trotter et al. |
| 4,221,887 A | 9/1980 | Brenner et al. |
| 4,229,337 A | 10/1980 | Brenner |
| 4,237,083 A | 12/1980 | Young et al. |
| 4,274,932 A | 6/1981 | Williams et al. |
| 4,288,358 A | 9/1981 | Trotter et al. |
| 4,288,480 A | 9/1981 | Grzywinski et al. |
| 4,289,668 A | 9/1981 | Li |
| 4,311,628 A | 1/1982 | Abdou-Sabet et al. |
| 4,321,334 A | 3/1982 | Chatterjee |
| 4,322,336 A | 3/1982 | Machurat et al. |
| 4,325,850 A | 4/1982 | Mueller |
| 4,327,007 A | 4/1982 | Vanderkooi, Jr. et al. |
| 4,335,026 A | 6/1982 | Balinth |
| 4,335,034 A | 6/1982 | Zuckerman et al. |
| 4,340,513 A | 7/1982 | Moteki et al. |
| 4,347,332 A | 8/1982 | Odorzynski et al. |
| 4,352,823 A | 10/1982 | Cherukuri et al. |
| 4,358,384 A | 11/1982 | Newcomb |
| 4,369,284 A | 1/1983 | Chen |
| 4,379,169 A | 4/1983 | Reggio et al. |
| 4,387,108 A | 6/1983 | Koch et al. |
| 4,399,248 A | 8/1983 | Singh et al. |
| 4,399,251 A | 8/1983 | Lee |
| 4,403,005 A | 9/1983 | Nevins et al. |
| 4,403,007 A | 9/1983 | Coughlin |
| 4,409,345 A | 10/1983 | Moteki et al. |
| 4,430,289 A | 2/1984 | McKinney et al. |
| 4,434,258 A | 2/1984 | Schumacher et al. |
| 4,438,228 A | 3/1984 | Schenck |
| 4,438,229 A | 3/1984 | Fujimori et al. |
| 4,440,829 A | 4/1984 | Gerace et al. |
| 4,450,250 A | 5/1984 | McConnell et al. |
| 4,452,820 A | 6/1984 | D'Amelia et al. |
| 4,459,311 A | 7/1984 | DeTora et al. |
| 4,460,729 A | 7/1984 | Books |
| 4,467,010 A | 8/1984 | Shii et al. |
| 4,467,065 A | 8/1984 | Williams et al. |
| 4,469,770 A | 9/1984 | Nelson |
| 4,483,952 A | 11/1984 | Uchiyama |
| 4,497,926 A | 2/1985 | Toy |
| 4,504,604 A | 3/1985 | Pilkington et al. |
| 4,518,615 A | 5/1985 | Cherukuri et al. |
| 4,529,666 A | 7/1985 | Salzburg et al. |
| 4,532,305 A | 7/1985 | Dickinson |
| 4,536,537 A | 8/1985 | Klingensmith et al. |
| 4,542,053 A | 9/1985 | Nevins et al. |
| 4,551,507 A | 11/1985 | Haylock et al. |
| 4,552,801 A | 11/1985 | Odorzynski et al. |
| 4,579,901 A | 4/1986 | Allen et al. |
| 4,584,215 A | 4/1986 | Bré et al. |
| 4,592,851 A | 6/1986 | Stadtmiller et al. |
| 4,616,052 A | 10/1986 | Habibullah |
| 4,645,791 A | 2/1987 | Theodore et al. |
| 4,659,757 A | 4/1987 | Okamoto et al. |
| 4,663,220 A | 5/1987 | Wisneski et al. |
| 4,666,959 A | 5/1987 | Weissberger et al. |
| 4,666,968 A | 5/1987 | Downey et al. |
| 4,670,341 A | 6/1987 | Lundsager |
| 4,684,682 A | 8/1987 | Lee, Jr. |
| 4,693,838 A | 9/1987 | Varma et al. |
| 4,703,078 A | 10/1987 | Machara et al. |
| 4,726,989 A | 2/1988 | Mrozinski |
| 4,745,143 A | 5/1988 | Mason et al. |
| 4,746,388 A | 5/1988 | Inaba et al. |
| 4,749,734 A * | 6/1988 | Williams et al. ............ 524/102 |
| 4,764,535 A | 8/1988 | Leicht |
| 4,772,657 A | 9/1988 | Akiyama et al. |
| 4,774,277 A | 9/1988 | Janac et al. |
| 4,814,375 A | 3/1989 | Esposito |
| 4,824,718 A | 4/1989 | Hwang |
| 4,824,891 A | 4/1989 | Laurent et al. |
| 4,833,172 A | 5/1989 | Schwarz et al. |
| 4,833,195 A | 5/1989 | Adur et al. |
| 4,840,988 A | 6/1989 | Nakayama et al. |
| 4,845,137 A | 7/1989 | Williams et al. |
| 4,853,428 A | 8/1989 | Theodore et al. |
| 4,857,646 A | 8/1989 | Jaffe |
| 4,863,785 A | 9/1989 | Berman et al. |
| 4,912,148 A | 3/1990 | Kim et al. |
| 4,914,145 A | 4/1990 | Tohdoh et al. |
| 4,919,992 A | 4/1990 | Blundell et al. |
| 4,939,040 A | 7/1990 | Oreglia et al. |
| 4,948,840 A | 8/1990 | Berta |
| 4,952,457 A | 8/1990 | Cartier et al. |
| 4,957,958 A | 9/1990 | Schleifstein |
| 4,959,285 A | 9/1990 | Hoffmann |
| 4,959,396 A | 9/1990 | Yankov et al. |
| 4,959,402 A | 9/1990 | Williams et al. |
| 4,960,820 A | 10/1990 | Hwo |
| 4,995,884 A | 2/1991 | Ross et al. |
| 4,996,094 A | 2/1991 | Dutt |
| 5,026,756 A | 6/1991 | Arendt |
| 5,028,647 A | 7/1991 | Haylock et al. |
| 5,049,605 A | 9/1991 | Rekers |
| 5,076,988 A | 12/1991 | Rifi |
| 5,079,287 A * | 1/1992 | Takeshi et al. ............... 524/528 |
| 5,080,942 A | 1/1992 | Yau |
| 5,091,454 A | 2/1992 | Arendt |
| 5,093,197 A | 3/1992 | Howard et al. |
| 5,105,038 A | 4/1992 | Chen et al. |
| 5,106,899 A | 4/1992 | Maresca |
| 5,114,763 A | 5/1992 | Brant et al. |
| 5,116,626 A | 5/1992 | Synosky et al. |
| 5,124,384 A | 6/1992 | Goldstein |
| 5,143,978 A | 9/1992 | Berta |
| 5,149,736 A | 9/1992 | Gamarra |
| 5,162,436 A | 11/1992 | Davis et al. |
| 5,171,908 A | 12/1992 | Rudnick |
| 5,173,317 A | 12/1992 | Hartman et al. |
| 5,180,865 A | 1/1993 | Heilman et al. |
| 5,206,276 A | 4/1993 | Lee, Jr. |
| 5,230,843 A | 7/1993 | Howard et al. |
| 5,231,128 A | 7/1993 | Nakata et al. |
| 5,238,735 A | 8/1993 | Nagou et al. |
| 5,240,966 A | 8/1993 | Iwasaki et al. |
| 5,250,628 A | 10/1993 | Seguela et al. |
| 5,254,378 A | 10/1993 | Krueger et al. |
| 5,256,717 A | 10/1993 | Stauffer et al. |
| 5,258,419 A | 11/1993 | Rolando et al. |
| 5,264,277 A | 11/1993 | Frognet et al. |
| 5,264,474 A | 11/1993 | Schleifstein et al. |
| 5,278,220 A | 1/1994 | Vermeire et al. |
| 5,286,500 A | 2/1994 | Synosky et al. |
| 5,290,886 A | 3/1994 | Ellul |
| 5,308,904 A | 5/1994 | Fujii et al. |
| 5,312,856 A | 5/1994 | Hert et al. |
| 5,324,580 A | 6/1994 | Allan et al. |
| 5,340,848 A * | 8/1994 | Asanuma et al. ............ 522/157 |
| 5,356,709 A | 10/1994 | Woo et al. |
| 5,356,948 A | 10/1994 | Payne, Jr. et al. |
| 5,356,986 A | 10/1994 | Stewart et al. |
| 5,360,868 A | 11/1994 | Mosier et al. |
| 5,376,716 A | 12/1994 | Nayak et al. |
| 5,389,711 A | 2/1995 | Westbrook et al. |

| | | | | | | |
|---|---|---|---|---|---|---|
| 5,397,832 | A | 3/1995 | Elul | 6,326,426 | B1 | 12/2001 | Ellul |
| 5,409,041 | A | 4/1995 | Yoshida et al. | 6,329,468 | B1 | 12/2001 | Wang |
| 5,412,020 | A | 5/1995 | Yamamoto et al. | 6,337,364 | B1 | 1/2002 | Sakaki et al. |
| 5,424,080 | A | 6/1995 | Synosky et al. | 6,342,209 | B1 | 1/2002 | Patil et al. |
| 5,437,877 | A | 8/1995 | Synosky et al. | 6,342,320 | B2 | 1/2002 | Liu et al. |
| 5,442,004 | A | 8/1995 | Sutherland et al. | 6,342,565 | B1 | 1/2002 | Cheng et al. |
| 5,459,193 | A | 10/1995 | Anderson et al. | 6,348,563 | B1 | 2/2002 | Fukuda et al. |
| 5,462,754 | A | 10/1995 | Synosky et al. | 6,362,252 | B1 | 3/2002 | Prutkin |
| 5,462,981 | A | 10/1995 | Bastioli et al. | 6,372,379 | B1 | 4/2002 | Samii et al. |
| 5,489,646 | A | 2/1996 | Tatman et al. | 6,380,292 | B1 | 4/2002 | Gibes et al. |
| 5,492,943 | A | 2/1996 | Stempel | 6,384,115 | B1 | 5/2002 | Van Gysel et al. |
| 5,512,625 | A | 4/1996 | Butterbach et al. | 6,403,692 | B1 | 6/2002 | Traugott et al. |
| 5,548,008 | A * | 8/1996 | Asanuma et al. ............... 524/99 | 6,410,200 | B1 | 6/2002 | Williams et al. |
| 5,552,482 | A | 9/1996 | Berta | 6,413,458 | B1 | 7/2002 | Pearce |
| 5,563,222 | A | 10/1996 | Fukuda et al. | 6,448,338 | B1 | 9/2002 | Born et al. |
| 5,569,693 | A | 10/1996 | Doshi et al. | 6,451,915 | B1 | 9/2002 | Ellul et al. |
| 5,591,817 | A | 1/1997 | Asanuma et al. | 6,465,109 | B2 | 10/2002 | Ohtsuka |
| 5,601,858 | A | 2/1997 | Mansukhani et al. | 6,482,281 | B1 | 11/2002 | Schmidt |
| 5,614,297 | A | 3/1997 | Velazquez | 6,498,213 | B2 | 12/2002 | Jeong et al. |
| 5,624,627 | A * | 4/1997 | Yagi et al. ................... 264/447 | 6,509,128 | B1 | 1/2003 | Everaerts et al. |
| 5,624,986 | A | 4/1997 | Bunnelle et al. | 6,515,231 | B1 | 2/2003 | Strobech et al. |
| 5,663,230 | A | 9/1997 | Haman | 6,531,214 | B2 | 3/2003 | Carter et al. |
| 5,683,634 | A | 11/1997 | Fujii et al. | 6,538,066 | B2 | 3/2003 | Watanabe et al. |
| 5,683,815 | A | 11/1997 | Leiss | 6,559,232 | B2 | 5/2003 | Inoue et al. |
| 5,688,850 | A | 11/1997 | Wyffels | 6,583,207 | B2 | 6/2003 | Stanhope et al. |
| 5,700,312 | A | 12/1997 | Fausnight et al. | 6,610,768 | B1 | 8/2003 | Jelenic et al. |
| 5,726,239 | A | 3/1998 | Maes et al. | 6,623,847 | B2 | 9/2003 | Yates |
| 5,728,760 | A | 3/1998 | Rose et al. | 6,632,974 | B1 | 10/2003 | Suzuki et al. |
| 5,736,197 | A | 4/1998 | Gaveske | 6,639,020 | B1 | 10/2003 | Brant |
| 5,739,200 | A | 4/1998 | Cheung et al. | 6,642,316 | B1 | 11/2003 | Datta et al. |
| 5,741,840 | A | 4/1998 | Lindquist et al. | 6,706,828 | B2 | 3/2004 | DiMaio |
| 5,747,573 | A | 5/1998 | Ryan | 6,720,376 | B2 | 4/2004 | Itoh et al. |
| 5,776,589 | A | 7/1998 | Mace et al. | 6,730,739 | B2 * | 5/2004 | Gipson ....................... 525/191 |
| 5,783,531 | A | 7/1998 | Andrew et al. | 6,753,373 | B2 | 6/2004 | Winowiecki |
| 5,786,418 | A | 7/1998 | Strelow et al. | 6,803,415 | B1 * | 10/2004 | Mikielski et al. ............ 525/191 |
| 5,789,529 | A | 8/1998 | Matsumura et al. | 6,867,253 | B1 | 3/2005 | Chen |
| 5,804,630 | A | 9/1998 | Heyer et al. | 6,905,760 | B1 | 6/2005 | Mukohara et al. |
| 5,837,769 | A | 11/1998 | Graafland et al. | 7,271,209 | B2 * | 9/2007 | Li et al. ...................... 524/284 |
| 5,849,806 | A | 12/1998 | St. Clair et al. | 2001/0051265 | A1 | 12/2001 | Williams et al. |
| 5,869,555 | A | 2/1999 | Simmons et al. | 2002/0049276 | A1 | 4/2002 | Zwick |
| 5,869,560 | A | 2/1999 | Kobayashi et al. | 2002/0077409 | A1 | 6/2002 | Sakaki et al. |
| 5,869,562 | A | 2/1999 | Lindquist et al. | 2002/0147266 | A1 | 10/2002 | Rawlinson et al. |
| 5,872,183 | A | 2/1999 | Bonnet et al. | 2002/0155267 | A1 | 10/2002 | Bader |
| 5,891,946 | A | 4/1999 | Nohara et al. | 2002/0160137 | A1 | 10/2002 | Varma |
| 5,908,421 | A | 6/1999 | Beger | 2002/0168518 | A1 | 11/2002 | Bond et al. |
| 5,916,959 | A | 6/1999 | Lindquist et al. | 2002/0183429 | A1 | 12/2002 | Itoh et al. |
| 5,929,147 | A | 7/1999 | Pierick et al. | 2002/0188057 | A1 | 12/2002 | Chen |
| 5,939,483 | A | 8/1999 | Kueppers | 2003/0004266 | A1 | 1/2003 | Kitazaki et al. |
| 5,948,557 | A | 9/1999 | Ondeck et al. | 2003/0022977 | A1 | 1/2003 | Hall |
| 5,968,455 | A * | 10/1999 | Brickley ..................... 422/121 | 2003/0032696 | A1 | 2/2003 | Sime et al. |
| 5,969,021 | A | 10/1999 | Reddy et al. | 2003/0035951 | A1 | 2/2003 | Magill et al. |
| 6,001,455 | A | 12/1999 | Nishio et al. | 2003/0036577 | A1 | 2/2003 | Hughes |
| 6,017,986 | A | 1/2000 | Burton | 2003/0091803 | A1 | 5/2003 | Bond et al. |
| 6,025,448 | A | 2/2000 | Swindoll et al. | 2003/0092826 | A1 | 5/2003 | Pearce |
| 6,027,674 | A | 2/2000 | Yates | 2003/0134552 | A1 | 7/2003 | Mehawej et al. |
| 6,042,902 | A | 3/2000 | Kuder et al. | 2003/0157859 | A1 | 8/2003 | Ishikawa |
| 6,045,922 | A | 4/2000 | Janssen et al. | 2003/0181575 | A1 | 9/2003 | Schmidt et al. |
| 6,060,561 | A | 5/2000 | Wolfschwenger et al. | 2003/0181584 | A1 | 9/2003 | Handlin, Jr. et al. |
| 6,077,899 | A | 6/2000 | Yatsuyanagi et al. | 2003/0187081 | A1 | 10/2003 | Cui |
| 6,084,031 | A | 7/2000 | Medsker et al. | 2004/0034148 | A1 | 2/2004 | Kelly et al. |
| 6,086,996 | A * | 7/2000 | Rancich et al. ....... 428/355 EN | 2004/0054040 | A1 | 3/2004 | Lin et al. |
| 6,090,081 | A * | 7/2000 | Sudo et al. ................. 604/230 | 2004/0063806 | A1 | 4/2004 | Kaarnakari |
| 6,111,039 | A * | 8/2000 | Miro et al. ................. 526/128 | 2004/0070653 | A1 | 4/2004 | Mashita et al. |
| 6,127,444 | A | 10/2000 | Kadri | 2004/0091631 | A1 | 5/2004 | Belli et al. |
| 6,143,818 | A | 11/2000 | Huang et al. | 2004/0106723 | A1 | 6/2004 | Yang et al. |
| 6,190,769 | B1 | 2/2001 | Wang | 2004/0116515 | A1 | 6/2004 | Anderson et al. |
| 6,191,078 | B1 | 2/2001 | Shlomo et al. | 2004/0186214 | A1 | 9/2004 | Li et al. |
| 6,194,498 | B1 | 2/2001 | Anderson et al. | 2004/0214498 | A1 | 10/2004 | Webb et al. |
| 6,197,285 | B1 | 3/2001 | Kowalik et al. | 2004/0249046 | A1 | 12/2004 | Abhari et al. |
| 6,231,936 | B1 | 5/2001 | Kozimor et al. | 2004/0260001 | A1 | 12/2004 | Lin et al. |
| 6,231,970 | B1 | 5/2001 | Andersen et al. | 2004/0266948 | A1 | 12/2004 | Jacob et al. |
| 6,271,294 | B1 | 8/2001 | Lasson et al. | 2005/0018983 | A1 | 1/2005 | Brown et al. |
| 6,316,068 | B1 | 11/2001 | Masubuchi et al. | 2005/0106978 | A1 | 5/2005 | Cheng et al. |

| | | | | | | |
|---|---|---|---|---|---|---|
| 2005/0148720 | A1 | 7/2005 | Li et al. | EP | 0 682 074 | 11/1995 |
| 2005/0170117 | A1 | 8/2005 | Cleveland et al. | EP | 0 699 519 | 3/1996 |
| 2005/0262464 | A1 | 11/2005 | Esch, Jr. et al. | EP | 0 716 124 | 6/1996 |
| 2005/0271851 | A1 | 12/2005 | Shibatou et al. | EP | 0 742 227 | 11/1996 |
| 2005/0277738 | A1 | 12/2005 | Hoyweghen et al. | EP | 0 755 970 | 1/1997 |
| 2006/0008643 | A1 | 1/2006 | Lin et al. | EP | 0 757 076 | 2/1997 |
| 2006/0079617 | A1 | 4/2006 | Kappes et al. | EP | 0 801 104 | 10/1997 |
| 2006/0100347 | A1 | 5/2006 | Ouhadi et al. | EP | 0 827 526 | 3/1998 |
| 2006/0135699 | A1 | 6/2006 | Li et al. | EP | 0 886 656 | 12/1998 |
| 2006/0167184 | A1 | 7/2006 | Waddell et al. | EP | 0 902 051 | 3/1999 |
| 2006/0173123 | A1 | 8/2006 | Yang et al. | EP | 0 940 433 | 9/1999 |
| 2006/0189763 | A1 | 8/2006 | Yang et al. | EP | 1 028 145 | 8/2000 |
| 2006/0205863 | A1 | 9/2006 | Lin et al. | EP | 1028145 | 8/2000 |
| 2007/0021560 | A1 | 1/2007 | Tse et al. | EP | 1 104 783 | 6/2001 |
| | | | | EP | 1 138 478 | 10/2001 |

FOREIGN PATENT DOCUMENTS

| | | | | | |
|---|---|---|---|---|---|
| EP | 1 201 391 | 5/2002 |
| EP | 1 211 285 | 6/2002 |
| DE | 1 282 942 | 11/1968 | EP | 1 214 386 | 6/2002 |
| DE | 1 961 981 | 7/1970 | EP | 1 252 231 | 10/2002 |
| DE | 1 669 261 | 10/1970 | EP | 1 331 258 | 7/2003 |
| DE | 1 921 649 | 11/1970 | EP | 1 342 249 | 1/2009 |
| DE | 2 019 945 | 11/1971 | FR | 1 167 244 | 11/1958 |
| DE | 2 108 293 | 3/1972 | FR | 1 536 425 | 7/1968 |
| DE | 1769723 | 10/1972 | FR | 1566388 | 3/1969 |
| DE | 26 32 957 | 1/1978 | FR | 1 580 539 | 9/1969 |
| DE | 32 44 499 | 6/1983 | FR | 2094870 | 2/1972 |
| DE | 37 35 502 | 5/1989 | FR | 2 110 824 | 6/1972 |
| DE | 39 11 725 | 10/1990 | FR | 2.212.382 | 7/1974 |
| DE | 44 17 191 | 8/1995 | FR | 2 256 207 | 12/1974 |
| DE | 37 35 502 | 5/1998 | FR | 2 272 143 | 5/1975 |
| DE | 198 41 303 | 3/2000 | FR | 2 590 910 | 6/1987 |
| DE | 19841303 | 3/2000 | FR | 2 602 515 | 2/1988 |
| EP | 0 039 126 | 11/1981 | GB | 0 511 319 | 8/1939 |
| EP | 0 083 049 | 7/1983 | GB | 0 511 320 | 8/1939 |
| EP | 0 087 294 | 8/1983 | GB | 964 845 | 7/1964 |
| EP | 0 097 969 | 1/1984 | GB | 1044028 | 9/1966 |
| EP | 0 046 536 | 1/1985 | GB | 1044502 | 10/1966 |
| EP | 0 050 548 | 1/1985 | GB | 1044503 | 10/1966 |
| EP | 0 058 331 | 6/1985 | GB | 1068783 | 5/1967 |
| EP | 0 058 404 | 1/1986 | GB | 1166664 | 10/1969 |
| EP | 0 210 733 | 2/1987 | GB | 1252638 | 11/1971 |
| EP | 0 214 112 | 3/1987 | GB | 1 331988 | 9/1973 |
| EP | 0 217 516 | 4/1987 | GB | 1329915 | 9/1973 |
| EP | 0 073 042 | 10/1987 | GB | 1452911 | 10/1976 |
| EP | 0 255 735 | 2/1988 | GB | 1458915 | 12/1976 |
| EP | 0 332 802 | 3/1988 | GB | 1559058 | 1/1980 |
| EP | 0 315 363 | 10/1988 | GB | 2 180 790 | 4/1987 |
| EP | 0 299 718 | 1/1989 | GB | 2 195 642 | 4/1988 |
| EP | 0 300 689 | 1/1989 | JP | 68013376 | 6/1943 |
| EP | 0300682 | 1/1989 | JP | 69029554 | 12/1966 |
| EP | 0300689 | 1/1989 | JP | 44029554 | 12/1969 |
| EP | 0 321 868 | 6/1989 | JP | 74-041101 | 11/1974 |
| EP | 0 322 169 | 6/1989 | JP | 50123148 | 9/1975 |
| EP | 0 315 481 | 8/1989 | JP | 50151243 | 12/1975 |
| EP | 0 343 943 | 11/1989 | JP | 76029170 | 3/1976 |
| EP | 0 369 164 | 5/1990 | JP | 53023388 | 3/1978 |
| EP | 0 389 695 | 10/1990 | JP | 53060383 | 5/1978 |
| EP | 0 407 098 | 1/1991 | JP | 53102381 | 9/1978 |
| EP | 0431475 | 6/1991 | JP | 56045932 | 4/1981 |
| EP | 0 448 259 | 9/1991 | JP | 56095938 | 8/1981 |
| EP | 477 748 A2 * | 9/1991 | JP | 60112439 | 6/1985 |
| EP | 448259 | 9/1991 | JP | 62132943 | 6/1987 |
| EP | 0 476 401 | 3/1992 | JP | 62223245 | 10/1987 |
| EP | 0 476 700 | 3/1992 | JP | 88033788 | 2/1988 |
| EP | 0 513 470 | 11/1992 | JP | 63251436 | 10/1988 |
| EP | 0315363 | 1/1994 | JP | 01016638 | 1/1989 |
| EP | 0 409 155 | 5/1994 | JP | 89017495 | 1/1989 |
| EP | 0 614 939 | 9/1994 | JP | 01066253 | 3/1989 |
| EP | 0 617 077 | 9/1994 | JP | 01/106628 | 4/1989 |
| EP | 0 622 432 | 11/1994 | JP | 1-192365 * | 8/1989 |
| EP | 0 428 153 | 3/1995 | JP | 01282280 | 11/1989 |
| EP | 0 664 315 | 7/1995 | JP | 02/038114 | 2/1990 |
| EP | 0 677 548 | 10/1995 | JP | 2067344 | 3/1990 |

| | | |
|---|---|---|
| JP | 03037481 | 2/1991 |
| JP | 03269036 | 11/1991 |
| JP | 04063851 | 2/1992 |
| JP | 04257361 | 9/1992 |
| JP | 05098088 | 4/1993 |
| JP | 5112842 | 5/1993 |
| JP | 05-202339 | 8/1993 |
| JP | 06-001892 | 1/1994 |
| JP | 06345893 | 12/1994 |
| JP | 95085907 | 3/1995 |
| JP | 07118492 | 5/1995 |
| JP | 07214685 | 8/1995 |
| JP | 07216143 | 8/1995 |
| JP | 07247387 | 9/1995 |
| JP | 07-292167 | 11/1995 |
| JP | 7292167 | 11/1995 |
| JP | 07292167 | 11/1995 |
| JP | 96019286 | 1/1996 |
| JP | 96019287 | 2/1996 |
| JP | 08034862 | 3/1996 |
| JP | 08246232 | 9/1996 |
| JP | 08269417 | 10/1996 |
| JP | 08333557 | 12/1996 |
| JP | 34 74677 | 1/1997 |
| JP | 09-076260 | 3/1997 |
| JP | 09 077901 | 3/1997 |
| JP | 9087435 | 3/1997 |
| JP | 09104801 | 4/1997 |
| JP | 9-208761 * | 8/1997 |
| JP | 09208761 | 8/1997 |
| JP | 9208761 | 8/1997 |
| JP | 10017693 | 1/1998 |
| JP | 10036569 | 2/1998 |
| JP | 2730079 | 3/1998 |
| JP | 10-168252 | 6/1998 |
| JP | 10158971 | 6/1998 |
| JP | 10279750 | 10/1998 |
| JP | 10324783 | 12/1998 |
| JP | 10325060 | 12/1998 |
| JP | 11020397 | 1/1999 |
| JP | 11 049 903 | 2/1999 |
| JP | 11060789 | 3/1999 |
| JP | 11080455 | 3/1999 |
| JP | 11239587 | 9/1999 |
| JP | 11291422 | 10/1999 |
| JP | 2000154281 | 6/2000 |
| JP | 2001064523 | 3/2001 |
| JP | 2001131509 | 5/2001 |
| JP | 2001233992 | 8/2001 |
| JP | 2001279501 | 10/2001 |
| JP | 2003142355 | 12/2001 |
| JP | 3325376 | 9/2002 |
| JP | 3325377 | 9/2002 |
| JP | 2004345327 | 12/2004 |
| SU | 455976 | 5/1975 |
| WO | 80/00028 | 1/1980 |
| WO | 89/08681 | 9/1989 |
| WO | WO 91/18045 | 11/1991 |
| WO | WO 92/14724 | 9/1992 |
| WO | WO 92/14784 | 9/1992 |
| WO | 92/16583 | 10/1992 |
| WO | 94/15014 | 7/1994 |
| WO | 95/13316 | 5/1995 |
| WO | 96/04419 | 2/1996 |
| WO | 96/11231 | 4/1996 |
| WO | 96/11232 | 4/1996 |
| WO | 96/26242 | 8/1996 |
| WO | 97/10298 | 3/1997 |
| WO | 97/19582 | 6/1997 |
| WO | 97/33921 | 9/1997 |
| WO | 98/36783 | 8/1998 |
| WO | 98/44041 | 10/1998 |
| WO | 98/46694 | 10/1998 |
| WO | WO 98/44041 * | 10/1998 |
| WO | WO 98/44041 A1 * | 10/1998 |
| WO | 99/13016 | 3/1999 |
| WO | WO 99/24501 | 5/1999 |
| WO | 99/62987 | 12/1999 |
| WO | WO 00/01745 | 1/2000 |
| WO | 00/66662 | 11/2000 |
| WO | 01/02263 | 1/2001 |
| WO | 01/18109 | 3/2001 |
| WO | WO 01/18109 | 3/2001 |
| WO | 01/43963 | 6/2001 |
| WO | 02/10310 | 2/2002 |
| WO | 02/17973 | 3/2002 |
| WO | 02/18487 | 3/2002 |
| WO | 02/30194 | 4/2002 |
| WO | 02/31044 | 4/2002 |
| WO | WO 02/30194 | 4/2002 |
| WO | WO 02/31044 | 4/2002 |
| WO | WO 02/31044 A1 * | 4/2002 |
| WO | 02/062891 | 8/2002 |
| WO | 02/072689 | 9/2002 |
| WO | 02/074873 | 9/2002 |
| WO | 02/088238 | 11/2002 |
| WO | WO 02/100153 | 12/2002 |
| WO | 03/029379 | 4/2003 |
| WO | 03/048252 | 6/2003 |
| WO | 03/060004 | 7/2003 |
| WO | 03/066729 | 8/2003 |
| WO | 2004/009699 | 1/2004 |
| WO | WO 2004/009699 | 1/2004 |
| WO | 2004/014997 | 2/2004 |
| WO | WO 2004/014998 | 2/2004 |
| WO | 2004/020195 | 3/2004 |
| WO | 2004/031292 | 4/2004 |
| WO | WO 2005/080495 | 9/2005 |
| WO | WO 2006/006346 | 1/2006 |
| WO | WO 2006/128467 | 12/2006 |
| WO | WO 2006/128646 | 12/2006 |

OTHER PUBLICATIONS

Dharmarajan, N. R.; Yu, T.C. Plastics Engineering, Aug. 1996, p. 33-35.*
EP 477 748 (Sep. 1991) abstract in English.*
JP 9-208761 (Aug. 1997) Tabata et al.; abstract and translation in English.*
Mitsui Petrochemicals LUCANT HC-40 Synthetic Oil product data sheet; Aug. 4, 2008.*
Abstract of JP 8253754, published on Oct. 1, 1996, entitled, "Method for Foaming Reactive Hot-Melt Polyurethane Adhesive".
PCT Written Opinion, Jan. 7, 2004, 2002B107B.
"Swelling Interaction, Plasticization, and Antioxidant extraction Between Fiber Optic Cable Gels and Polyolefins" B. G. Risch, Ph.D., SPE-ANTEC, 1999.
"Use of "Clean" Paraffinic Processing Oils to Improve TPE Properties", B. J. Gedeon et al., TPEs, 2000, pp. 157-170.
"Plasticizing of isotactic polypropylene upon addition of hydrocarbon oils", K. Nitta et al., e-Polymers, No. 021, 2004, pp. 1-11.
"The Effect of Oil Type and Content on the Rheological, Mechanical, and Thermal Properties of a Polyolefinic Based Thermoplastic Elastomer", McShane, et al. SPE-ANTEC, 2002.
Abstract of "Plasticizing Characteristics of High-Density Polyethylene" Wu et al., Suliao, 1988, 17 (4), 3-8.
Abstract of "Effect of Technological Additives on Properties of Thermoplastic vulcanizates Based on Ethylene Propylene Rubber and Polyolefins" Kanauzov et al., Kauchuk i Rezina, 2000, (4), 12-15.
Abstract of Polybutenes: a versatile modifier for plastics, J. D. Fotheringham, AddCon Asia (RAPRA), International Plastics Additives and Modifiers Conference, Singapore, Oct. 28-29, 1997.
Abstract of "Effect of Petroleum Plasticizers and Synthetic Oils on Rheological and service Properties of Polyolefins", M.D. Nasibova et al., Olefinov s Opyt. Z-dom, 1991 (14), 60-6.

"Rubber Chemicals and Additives", Rubber Technology Handbook, 1989, Werner Hoffman, Hanser Publishers, New York, pp. 294-305.

"Plasticizers", Additives for Plastics, J. Stepek, H. Daoust, 1983, Springer Verlag, New York, pp. 6-69.

"Lubricants and Other Processing Aids", Chemical Additives for the Plastics Industry, Properties, Applications, Toxicologies, Noyes Data Corporation, Park Ridge, NJ, 1987, pp. 1073116.

"Synthetic Lubricants and High-Performance Functional Fluids: Chemistry, Technology, and Commercial Importance", "Polybutenes", Second Edition, Rudnick, Shubkin, eds., Marcel Dekker, Inc. New York, 1999, pp. 1-52, 357-392.

Radian Corporation, "Plasticizers", Chemical Additives for the Plastics Industry, Noyes Data Corporation, NJ pp. 107-116, 1987.

Rudnick, L, et al.; Synthetic Lubricants and High-Performance Functional Fluids Second Edition, Revised and Expanded, Marcel Dekker, Inc., pp. 409-411, 1999.

U.S. Appl. No. 11/118,925, filed Apr. 29, 2005.

U.S. Appl. No. 60/649,107.

U.S. Appl. No. 60/649,264.

U.S. Appl. No. 60/649,266, filed Feb. 2, 2005, Wang et al.

U.S. Appl. No. 60/699,718, filed Jul. 15, 2005.

Khungar, S.L.; "Flexible Films of Polypropylene Plasticized with Polybutenes", Amoco Chemicals, pp. 2992-2996, 1996.

Pratt, C. F. et al.; "Control of Phase Separation and Voiding in Oil-Filled Polypropylene", Journal of Applied Polymers Science, Vo. 18, pp. 3621-3631, 1974.

Nitta, K. et al.; "Plasticizing of isotactic polypropylene upon addition of hydrocarbon oils", e-Polymers, vol. 021, pp. 1-11, 2004.

Gedeon, B. et al.; "Use of "Clean" Paraffinic Processing Oils to Improve", Paralux Articles, Presented at TPEs 2000, pp. 1-10, 2000.

Hawley's Condensed Chem. Dic., $14^{th}$ Ed. (2001), p. 835.

Parapol 450: Product information and data sheet, found online at: http://www.infochems.com/chemdb/product_content.asp?product_id=42969.

Parapol 950: Product information and data sheet, found online at: http://www.infochems.com/chemdb/product_content.asp?product_id=42981&1type=search&list=all&inx=all&search_option=trade_name&search_keyword=parapol%20950&lorder=regi_date&page=1.

Maier, C.; Calafut, T. (1998), Propylene—The Definitive User's Guide and Databook, (pp. 11-25 and 97-106), William Andrew Publishing/Plastics Design Library, Online version available at: http://www.knovel.com/knovel2/Toc.jsp?BookID=54&VerticalID=0.

Jens Stehr, Investigation of the Effects of Poly(α-olefin) Plasticizers on the Properties of Elastomers, KGK, Jan./Feb. 2007, pp. 14-19 (translated from German by McElroy Translation Company.

* cited by examiner

PLASTICIZED POLYOLEFIN COMPOSITIONS

CROSS REFERENCE TO RELATED APPLICATIONS

This application claims the benefit of U.S. Provisional Application Ser. No. 60/544,108 filed on Feb. 12, 2004. This application is also a continuation in part of U.S. Ser. No. 10/640,435, filed Aug. 12, 2003 which claims the benefit of provisional application U.S. Ser. No. 60/402,665 filed on Aug. 12, 2002. This application is also a continuation in part of U.S. Ser. No. 10/634,351 filed Aug. 4, 2003 which claims the benefit of provisional application U.S. Ser. No. 60/402,665 filed on Aug. 12, 2002.

FIELD OF THE INVENTION

The present invention relates to radiation resistant plasticized polyolefins comprising a polyolefin and a non-functionalized plasticizer and articles produced therefrom.

BACKGROUND OF THE INVENTION

Polyolefins are useful in any number of everyday articles. However, one drawback to many polyolefins, especially propylene homopolymers and some propylene copolymers, is their relatively high glass transition temperature. This characteristic makes these polyolefins brittle, especially at low temperatures. Many applications of polyolefins benefit from having useful properties over a broad range of temperatures; consequently, there is a need to provide polyolefins that can maintain desirable characteristics such as high or low temperature performance, etc., while maintaining or improving upon the impact strength and toughness at lower temperatures. In particular, it would be advantageous to provide a propylene polymer possessing improved toughness and or high use temperature without sacrificing its other desirable properties.

Addition of a plasticizer or other substance to a polyolefin is one way to improve such properties as impact strength and toughness. Some patent disclosures directed to such an end are U.S. Pat. No. 4,960,820; U.S. Pat. No. 4,132,698; U.S. Pat. No. 3,201,364; WO 02/31044; WO 01/18109 A1; and EP 0 300 689 A2. These disclosures are directed to polyolefins and elastomers blended with functionalized plasticizers. The functionalized plasticizers are materials such as mineral oils which contain aromatic groups, and high (greater than −20° C.) pour point compounds. Use of these compounds typically does not preserve the transparency of the polyolefin, and impact strength is often not improved.

WO 98/44041 discloses plastic based sheet like material for a structure, especially a floor covering, which contains in a blend a plastic matrix comprising a chlorine free polyolefin or mixture of polyolefins and a plasticizer characterized in that the plasticizer is an oligomeric polyalphaolefin type substance.

Other background references include EP 0 448 259 A, EP 1 028 145 A, U.S. Pat. Nos. 4,073,782, and 3,415,925.

What is needed is a polyolefin with lower flexural modulus, lower glass transition temperature, and higher impact strength near and below 0° C., while not materially influencing the peak melting temperature of the polyolefin, the polyolefin crystallization rate, or its clarity, and with minimal migration of plasticizer to the surface of fabricated articles. A plasticized polyolefin according to this invention can fulfill these needs. More specifically, there is a need for a plasticized polypropylene that can be used in such applications as food containers, medical devices, durable household goods, and toys.

Likewise, a plasticized polyolefin with improved softness, better flexibility (especially lower flexural modulus), a depressed glass transition temperature, and/or improved impact strength (especially improved Gardner impact), where the melting temperature of the polyolefin, the polyolefin crystallization rate, or its optical properties (especially clarity and color) are not influenced and with minimal migration of the plasticizer to the surface of articles made therefrom is desirable.

It would be particularly desirable to plasticize polyolefins by using a simple, non-reactive compound such as a paraffin. However, it has been taught that aliphatic or paraffinic compounds would impair the properties of polyolefins, and was thus not recommended. (See, e.g., CHEMICAL ADDITIVES FOR PLASTICS INDUSTRY 107-116 (Radian Corp., Noyes Data Corporation, NJ 1987); WO 01/18109 A1).

Mineral oils, which have been used as extenders, softeners, and the like in various applications, consist of thousands of different compounds, many of which are undesirable in a lubricating system. Under moderate to high temperatures these compounds can volatilize and oxidize, even with the addition of oxidation inhibitors.

Certain mineral oils, distinguished by their viscosity indices and the amount of saturates and sulfur they contain, have been classified as Hydrocarbon Basestock Group I, II or III by the American Petroleum Institute (API). Group I basestocks are solvent refined mineral oils. They contain the most unsaturates and sulfur and have the lowest viscosity indices. They define the bottom tier of lubricant performance. Group I basestocks are the least expensive to produce, and they currently account for abut 75 percent of all basestocks. These comprise the bulk of the "conventional" basestocks. Groups II and III are the High Viscosity Index and Very High Viscosity Index basestocks. They are hydroprocessed mineral oils. The Group III oils contain less unsaturates and sulfur than the Group I oils and have higher viscosity indices than the Group II oils do. Additional basestocks, named Groups IV and V, are also used in the basestock industry. Rudnick and Shubkin (*Synthetic Lubricants and High-Performance Functional Fluids*, Second edition, Rudnick, Shubkin, eds., Marcel Dekker, Inc. New York, 1999) describe the five basestock Groups as typically being:

Group I—mineral oils refined using solvent extraction of aromatics, solvent dewaxing, hydrofining to reduce sulfur content to produce mineral oils with sulfur levels greater than 0.03 weight %, saturates levels of 60 to 80% and a viscosity index of about 90;

Group II—mildly hydrocracked mineral oils with conventional solvent extraction of aromatics, solvent dewaxing, and more severe hydrofining to reduce sulfur levels to less than or equal to 0.03 weight % as well as removing double bonds from some of the olefinic and aromatic compounds, saturate levels are greater than 95-98% and VI is about 80-120;

Group III—severely hydrotreated mineral oils with saturates levels of some oils virtually 100%, sulfur contents are less than or equal to 0.03 weight % (preferably between 0.001 and 0.01%) and VI is in excess of 120;

Group IV—poly(alpha-olefin) hydrocarbons manufactured by the catalytic oligomerization of linear olefins having 6 or more carbon atoms. In industry however, the Group IV basestocks are referred to as "polyalphaolefins" are generally thought of as a class of synthetic basestock fluids produced by oligomerizing $C_4$ and greater alphaolefins;

and

Group V—esters, polyethers, polyalkylene glycols, and includes all other basestocks not included in Groups I, II, III and IV.

Other references of interest include: U.S. Pat. No. 5,869,555, U.S. Pat. No. 4,210,570, U.S. Pat. No. 4,110,185, GB 1,329,915, U.S. Pat. No. 3,201,364, U.S. Pat. No. 4,774,277, JP01282280, FR2094870, JP69029554, *Rubber Technology Handbook*, Werner Hoffman, Hanser Publishers, New York, 1989, pg294-305, *Additives for Plastics*, J. Stepek, H. Daoust, Springer Verlag, New York, 1983, pg-6-69.

U.S. Pat. No. 4,536,537 discloses blends of LLDPE (UC 7047), polypropylene (5520) and Synfluid 2CS, 4CS, or 6CS having a viscosity of 4.0 to 6.5 cSt at 100° F./38° C., however the Synfluid 4CS and 8CS are reported to "not work" (col 3, ln 12).

In another aspect is also desirable to have flexible polyolefins (typically polypropylene) that can withstand sterilizing amounts of radiation. Typical polypropylene tends to soften and deform when sterilized at high temperature by steam or turn yellow and/or become brittle when treated with high energy radiation, particularly beta and gamma radiation.

Beta radiation, such as from an electron beam, or gamma radiation, such as from a cobalt-60 source, is often used to sterilize medical equipment. This is a particularly convenient means of sterilization since the items may be packed in bulk, or in individually sealed clean packages, and irradiated after packaging. Such treatments yield sterile instruments and devices without the need for special handling or repackaging after sterilization. Thus, sterility and enhanced patient safety are assured. However, because polypropylene tends to degrade when exposed to sterilizing levels of radiation, such treatment is generally inappropriate for medical devices incorporating polypropylene components or for medical devices packaged in polypropylene containers.

But for this limitation, polypropylene would be very useful for making a tremendous number of useful items including syringe barrels, culture dishes, tissue culture bottles, intravenous catheters and tubing, and bags or bottles, surgical probes, suture material, and other goods.

The potential usefulness of polypropylene has been recognized for some time. Others in the field have attempted to overcome the property limitations by numerous means. In U.S. Pat. No. 4,110,185, for example, Williams, Dunn, and Stannett describe the use of a non-crystalline mobilizing agent in polypropylene formulations to increase the free volume of the polymer and prevent radiation embrittlement (see also U.S. Pat. No. 4,274,932 and U.S. Pat. No. 4,467,065). In U.S. Pat. No. 4,845,137, Williams and Titus describe a polypropylene composition which is stable to sterilizing radiation, comprising polypropylene of narrow molecular weight distribution (Mw/Mn), a liquid mobilizing additive, a hindered amine compound, and a clarifying agent. While these additives generally appear to enhance radiation-tolerance, mobilizing additives tend to be oily or greasy. This can contribute to processing difficulties and product flaws.

Other inventions attempting to stabilize polypropylene against the effects of high energy radiation employ syndiotactic polypropylene. EP-A2-0 431 475, describes making a radiation resistant polypropylene resin composition suitable for the preparation of molded articles in which physical properties "scarcely deteriorate during sterilization by radiation" by utilizing substantially syndiotactic polypropylene. The composition may also include a phosphorous containing anti-oxidant, an amine containing antioxidant, and a nucleating agent.

JP 04-214709 apparently describes ethylene/propylene copolymers with at least 50% syndiotacticity which have improved radiation tolerance. Such copolymers are produced by specific chiral metallocene-type catalysis and are preferably compounded with phosphorous or amine-containing antioxidants for best radiation tolerance.

U.S. Pat. No. 5,340,848 describes a radiation resistant polypropylene resin composition comprising a polypropylene having a substantially syndiotactic structure with optional anti-oxidants and/or nucleating agents.

WO 92/14784 describes blends of from 30 to 40 weight percent of an ethylene-based copolymer with 70 to 30 weight percent of a propylene-based copolymer for use in heat seal applications.

These references indicate that a simple, cost effective system to provide radiation tolerant polypropylene has long been sought. Ideally, such a polypropylene composition would provide products that are clear and would be dimensionally stable at elevated temperatures. Such products could optionally be subjected to sterilization by means other than radiation without softening or deformation or significant deterioration of optical and or strength properties. It would further benefit the makers of polypropylene articles if the polymer blend used for forming would not tend to foul the molding equipment with oil or grease. Users of the final formed products, as well as makers of such articles, would benefit if such polymer compounds would not exude oil or grease from the surface of molded parts, films, or packaging. Such articles would be particularly attractive to the medical and food packaging industries.

SUMMARY OF THE INVENTION

This invention relates to sterilized articles comprising polypropylene and a non-functionalized plasticizer and processes to sterilize such articles.

This invention relates to sterilized articles comprising plasticized polyolefin compositions comprising one or more polyolefins and one or more non-functionalized plasticizers ("NFP").

This invention relates to a sterilized article comprising a plasticized polyolefin composition comprising one or more polyolefins and one or more non-functionalized plasticizers where the non-functionalized plasticizer comprises $C_{20}$ to $C_{1500}$ paraffins having a kinematic viscosity of 5 cSt or more at 100° C. and a viscosity index of 120 or more, wherein the article has been subjected to an amount of radiation sufficient to sterilize the article.

DEFINITIONS

For purposes of this invention and the claims thereto when a polymer or oligomer is referred to as comprising an olefin, the olefin present in the polymer or oligomer is the polymerized or oligomerized form of the olefin, respectively. Likewise the use of the term polymer is meant to encompass homopolymers and copolymers. In addition the term copolymer includes any polymer having 2 or more monomers. Thus, as used herein, the term "polypropylene" means a polymer made of at least 50% propylene units, preferably at least 70% propylene units, more preferably at least 80% propylene units, even more preferably at least 90% propylene units, even more preferably at least 95% propylene units or 100% propylene units.

For purposes of this invention an oligomer is defined to have a number-average molecular weight ($M_n$) of less than 21,000 g/mol, preferably less than 20,000 g/mol, preferably less than 19,000 g/mol, preferably less than 18,000 g/mol, preferably less than 16,000 g/mol, preferably less than 15,000 g/mol, preferably less than 13,000 g/mol, preferably less than 10,000 g/mol, preferably less than 5000 g/mol, preferably less than 3000 g/mol.

For purposes of this invention and the claims thereto Group I, II, and III basestocks are defined to be mineral oils having the following properties:

|  | Saturates (wt %) | Sulfur (wt %) | Viscosity Index |
|---|---|---|---|
| Group I | <90 &/or | >0.03% & | ≧80 & <120 |
| Group II | ≧90 & | ≦0.03% & | ≧80 & <120 |
| Group III | ≧90 & | ≦0.03% & | ≧120 |

DETAILED DESCRIPTION OF THE INVENTION

This invention relates to plasticized polyolefin compositions comprising one or more polyolefins and one or more non-functionalized plasticizers ("NFP").

Typically, the polyolefin(s) are present in the compositions of the present invention at from 40 wt % to 99.9 wt % (based upon the weight of the polyolefin and the NFP) in one embodiment, and from 50 wt % to 99 wt % in another embodiment, and from 60 wt % to 98 wt % in yet another embodiment, and from 70 wt % to 97 wt % in yet another embodiment, and from 80 wt % to 97 wt % in yet another embodiment, and from 90 wt % to 98 wt % in yet another embodiment, wherein a desirable range may be any combination of any upper wt % limit with any lower wt % limit described herein.

In another embodiment the plasticized polyolefin comprises polypropylene present at 40 to 99.99 weight %, alternately 50 to 99 weight %, alternately 60 to 99 weight %, alternately 70 to 98 weight %, alternately 80 to 97 weight %, alternately 90 to 96 weight %, and the NFP is present at 60 to 0.01 weight %, alternately 50 to 1 weight %, alternately 40 to 1 weight %, alternately 30 to 2 weight %, alternately 20 to 3 weight %, alternately 10 to 4 weight %, based upon the weight of the polypropylene and the NFP.

In another embodiment the plasticized polyolefin comprises polybutene present at 50 to 99.99 weight %, alternately 60 to 99 weight %, alternately 70 to 98 weight %, alternately 80 to 97 weight %, alternately 90 to 96 weight %, and the NFP is present at 50 to 0.01 weight %, alternately 40 to 1 weight %, alternately 30 to 2 weight %, alternately 20 to 3 weight %, alternately 10 to 4 weight %, based upon the weight of the polybutene and the NFP.

In another embodiment the polyolefin comprises polypropylene and or polybutene and NFP is present at 0.01 to 50 weight %, more preferably 0.05 to 45 weight %, more preferably 0.5 to 40 weight %, more preferably 1 to 35 weight %, more preferably 2 to 30 weight %, more preferably 3 to 25 weight %, more preferably 4 to 20 weight %, more preferably 5 to 15 weight %, based upon the weight of the polypropylene and the NFP. In another embodiment, the NFP is present at 1 to 15 weight %, preferably 1 to 10 weight %, based upon the weight of the polypropylene and or polybutene and the NFP.

In another embodiment the NFP is present at more than 3 weight %, based upon the weight of the polyolefin and the NFP.

For purposes of this invention and the claims thereto the amount of NFP in a given composition is determined by the Extraction method described below. The CRYSTAF method also described is for comparison purposes.

For purposes of this invention and the claims thereto when melting point is referred to and there is a range of melting temperatures, the melting point is defined to be the peak melting temperature from a differential scanning calorimetry (DSC) trace as described below.

Non-Functionalized Plasticizer

The polyolefin compositions of the present invention include a non-functionalized plasticizer ("NFP"). The NFP of the present invention is a compound comprising carbon and hydrogen, and does not include to an appreciable extent functional groups selected from hydroxide, aryls and substituted aryls, halogens, alkoxys, carboxylates, esters, carbon unsaturation, acrylates, oxygen, nitrogen, and carboxyl. By "appreciable extent", it is meant that these groups and compounds comprising these groups are not deliberately added to the NFP, and if present at all, are present at less than 5 wt % by weight of the NFP in one embodiment, more preferably less than 4 weight %, more preferably less than 3 weight %, more preferably less than 2 weight %, more preferably less than 1 weight %, more preferably less than 0.7 weight %, more preferably less than 0.5 weight %, more preferably less than 0.3 weight %, more preferably less than 0.1 weight %, more preferably less than 0.05 weight %, more preferably less than 0.01 weight %, more preferably less than 0.001 weight %, based upon the weight of the NFP.

In a preferred embodiment the NFP comprises polyalphaolefins (PAO's) comprising oligomers of linear olefins having 5 to 14 carbon atoms, more preferably 6 to 14 carbon atoms, more preferably 8 to 12 carbon atoms, more preferably 10 carbon atoms having a kinematic viscosity of 5 or more (as measured by ASTM D 445), preferably 10 or more; and preferably having a viscosity index ("VI") of 120 or more (as measured by ASTM D 2270), more preferably 130 or more, more preferably 140 or more; and/or having a pour point of −5° C. or less (as measured by ASTM D 97), more preferably −10° C. or less, more preferably −20° C. or less.

In another embodiment polyalphaolefin oligomers useful in the present invention comprise $C_{20}$ to $C_{1500}$ paraffins, preferably $C_{40}$ to $C_{1000}$ paraffins, preferably $C_{50}$ to $C_{750}$ paraffins, preferably $C_{50}$ to $C_{500}$ paraffins. The PAO oligomers are dimers, trimers, tetramers, pentamers, etc. of $C_5$ to $C_{14}$ α-olefins in one embodiment, and $C_6$ to $C_{12}$ α-olefins in another embodiment, and $C_8$ to $C_{12}$ α-olefins in another embodiment. Suitable olefins include 1-pentene, 1-hexene, 1-heptene, 1-octene, 1-nonene, 1-decene, 1-undecene and 1-dodecene. In one embodiment, the olefin is 1-decene, and the NFP is a mixture of dimers, trimers, tetramers and pentamers (and higher) of 1-decene. Preferred PAO's are described more particularly in, for example, U.S. Pat. No. 5,171,908, and U.S. Pat. No. 5,783,531 and in SYNTHETIC LUBRICANTS AND HIGH-PERFORMANCE FUNCTIONAL FLUIDS pgs. 1-52 (Leslie R. Rudnick & Ronald L. Shubkin, ed. Marcel Dekker, Inc. 1999).

PAO's useful in the present invention typically possess a number-average molecular weight ($M_n$) of from 100 to 21,000 in one embodiment, and from 200 to 10,000 in another embodiment, and from 200 to 7,000 in yet another embodiment, and from 200 to 2,000 in yet another embodiment, and from 200 to 500 in yet another embodiment. Preferred PAO's have viscosities in the range of 5 to 150 cSt at 100° C., and from 5 to 3000 cSt at 100° C. in another embodiment (ASTM 445). PAO's useful in the present invention typically have pour points of less than 0° C. in one embodiment, less than −10° C. in another embodiment, and less than −20° C. in yet another embodiment, and less than −40° C. in yet another embodiment. Desirable PAO's are commercially available as SHF and SuperSyn PAO's (ExxonMobil Chemical Company, Houston Tex.), some of which are summarized in the Table 2 below.

TABLE 2

SHF and SuperSyn Series Polyalphaolefins

| PAO | specific gravity (15.6/15.6° C.) | kinematic viscosity @ 100° C., cSt | VI | pour point, ° C. |
|---|---|---|---|---|
| SHF-20 | 0.798 | 1.68 | — | −63 |
| SHF-21 | 0.800 | 1.70 | — | −57 |
| SHF-23 | 0.802 | 1.80 | — | −54 |
| SHF-41 | 0.818 | 4.00 | 123 | −57 |
| SHF-61/63 | 0.826 | 5.80 | 133 | −57 |
| SHF-82/83 | 0.833 | 7.90 | 135 | −54 |
| SHF-101 | 0.835 | 10.0 | 136 | −54 |
| SHF-403 | 0.850 | 40.0 | 152 | −39 |
| SHF-1003 | 0.855 | 107 | 179 | −33 |
| SuperSyn 2150 | 0.850 | 150 | 214 | −42 |
| SuperSyn 2300 | 0.852 | 300 | 235 | −30 |
| SuperSyn 21000 | 0.856 | 1,000 | 305 | −18 |
| SuperSyn 23000 | 0.857 | 3,000 | 388 | −9 |

Other useful PAO's include those sold under the tradenames Synfluid™ available from ChevronPhillips Chemical Co. in Pasedena Tex., Durasyn™ available from BP Amoco Chemicals in London England, Nexbase™ available from Fortum Oil and Gas in Finland, Synton™ available from Crompton Corporation in Middlebury Conn., USA, EMERY™ available from Cognis Corporation in Ohio, USA.

In other embodiments the PAO's have a kinematic viscosity of 10 cSt or more at 100° C., preferably 30 cSt or more, preferably 50 cSt or more, preferably 80 cSt or more, preferably 110 or more, preferably 150 cSt or more, preferably 200 cSt or more, preferably 500 cSt or more, preferably 750 or more, preferably 1000 cSt or more, preferably 1500 cSt or more, preferably 2000 cSt or more, preferably 2500 cSt or more. In another embodiment the PAO's have a kinematic viscosity at 100° C. of between 10 cSt and 3000 cSt, preferably between 10 cSt and 1000 cSt, preferably between 10 cSt and 40 cSt.

In other embodiments the PAO's have a viscosity index of 120 or more, preferably 130 or more, preferably 140 or more, preferably 150 or more, preferably 170 or more, preferably 190 or more, preferably 200 or more, preferably 250 or more, preferably 300 or more.

In a particularly preferred embodiment the PAO has a kinematic viscosity of 10 cSt or more at 100° C. when the polypropylene is RB 501 F, Hifax CA12A, or ADFLEX Q 100F, as these polymers are described in WO 98/44041.

This invention also relates to plasticized polyolefin compositions comprising one or more polyolefins and one or more non-functionalized plasticizers where the non-functionalized plasticizer comprises a high purity hydrocarbon fluid composition comprising a mixture of paraffins having 6 to 1500 carbon atoms, preferably 8 to 1000 carbon atoms, preferably 10 to 500 carbon atoms, preferably 12 to about 200 carbon atoms, preferably 14 to 150 carbon atoms, preferably 16 to 100 carbon atoms in the molecule. The hydrocarbon fluid composition has an isoparaffin:n-paraffin ratio ranging from about 0.5:1 to about 9:1, preferably from about 1:1 to about 4:1. The isoparaffins of the mixture contain greater than fifty percent, 50%, mono-methyl species, e.g., 2-methyl, 3-methyl, 4-methyl, ≧5-methyl or the like, with minimum formation of branches with substituent groups of carbon number greater than 1, i.e., ethyl, propyl, butyl or the like, based on the total weight of isoparaffins in the mixture. Preferably, the isoparaffins of the mixture contain greater than 70 percent of the mono-methyl species, based on the total weight of the isoparaffins in the mixture. These hydrocarbon fluids preferably have kinematic viscosities (KV) at 25° C. ranging from 1 to 100,000 cSt, preferably 10 cSt to 2000 cSt and, optionally low pour points typically below −20° C., more preferably below −30° C., more preferably ranging from about −20° C. to about −70° C. These hydrocarbon fluids preferably have kinematic viscosities at 40° C. ranging from 1 to 30,000 cSt, preferably 10 cSt to 2000 cSt and, optionally low pour points typically below −20° C., more preferably below −30° C., more preferably ranging from about −20° C. to about −70° C.

This invention also relates to plasticized polyolefin compositions comprising one or more polyolefins and one or more non-functionalized plasticizers where the non-functionalized plasticizer comprises a linear or branched paraffinic hydrocarbon composition having:
1. a number average molecular weight of 500 to 21,000 g/mol;
2. less than 10% sidechains having 4 or more carbons, preferably less than 8 weight %, preferably less than 5 weight %, preferably less than 3 weight %, preferably less than 2 weight %, preferably less than 1 weight %, preferably less than 0.5 weight %, preferably less than 0.1 weight %, preferably at less than 0.1 weight %, preferably at 0.001 weight %;
3. at least 1 or 2 carbon branches present at 15 weight % or more, preferably 20 weight % or more, preferably 25 weight % or more, preferably 30 weight % or more, preferably 35 weight % or more, preferably 40 weight % or more, preferably 45 weight % or more, preferably 50 weight % or more,
4. less than 2.5 weight % cyclic paraffins, preferably less than 2 weight %, preferably less than 1 weight %, preferably less than 0.5 weight %, preferably less than 0.1 weight %, preferably at less than 0.1 weight %, preferably at 0.001 weight %. In additional embodiments these NFP's have a kinematic viscosity 2cSt or more at 100° C. and or a VI of 120 or more, preferably 130 or more, preferably 140 or more, preferably 150 or more, preferably 170 or more, preferably 190 or more, preferably 200 or more, preferably 250 or more, preferably 300 or more.

In another embodiment, the NFP comprises a high purity hydrocarbon fluid composition which comprises a mixture of paraffins of carbon number ranging from about $C_8$ to $C_{20}$, has a molar ratio of isoparaffins:n-paraffins ranging from about 0.5:1 to about 9:1, the isoparaffins of the mixture contain greater than 50 percent of the mono-methyl species, based on the total weight of the isoparaffins of the mixture and wherein the composition has pour points ranging from about −20° F. to about −70° F., and kinematic viscosities at 25° C. ranging from about 1 cSt to about 10 cSt.

In another embodiment, the mixture of paraffins has a carbon number ranging from about $C_{10}$ to about $C_{16}$. In another embodiment, the mixture contains greater than 70 percent of the mono-methyl species. In another embodiment, the mixture boils at a temperature ranging from about 320° F. to about 650° F. In another embodiment, the mixture boils within a range of from about 350° F. to about 550° F. In another embodiment, the mixture comprises a mixture of paraffins of carbon number ranging from about $C_{10}$ to about $C_{16}$. In another embodiment, the mixture is of carbon numbers ranging from about $C_{10}$-$C_{16}$, the mixture contains greater than 70 percent of the mono-methyl species and boils within a range of from about 350° F. to about 550° F. In another embodiment, the mixture has a molar ratio of isoparaffins:n- paraffins ranging from about 1:1 to about 4:1. In another embodiment, the mixture is derived from a Fischer-Tropsch process. Such NFP's may be produced by the methods disclosed in U.S. Pat. No. 5,906,727.

Any of the NFP's may also be described by any number of, or any combination of, parameters described herein. In one embodiment, any of the NFP's of the present invention has a pour point (ASTM D97) of from less than 0° C. in one embodiment, and less than −5° C. in another embodiment, and less than −10° C. in another embodiment, less than −20° C. in yet another embodiment, less than −40° C. in yet another embodiment, less than −50° C. in yet another embodiment, and less than −60° C. in yet another embodiment, and greater than −120° C. in yet another embodiment, and greater than −200° C. in yet another embodiment, wherein a desirable range may include any upper pour point limit with any lower pour point limit described herein. In one embodiment, the NFP is a paraffin or other compound having a pour point of less than −30° C., and between −30° C. and −90° C. in another embodiment, in the kinematic viscosity range of from 0.5 to 200 cSt at 40° C. Most mineral oils, which typically include aromatic moieties and other functional groups, have a pour point of from 10° C. to −20° C. at the same viscosity range.

In another embodiment any NFP described herein may have a viscosity index (VI) of 120 or more, more preferably 125 or more, more preferably 130 or more. In another embodiment the NFP has a VI between 90 and 400, preferably between 120 and 350.

Any NFP described herein may have a dielectric constant at 20° C. of less than 3.0 in one embodiment, and less than 2.8 in another embodiment, less than 2.5 in another embodiment, and less than 2.3 in yet another embodiment, and less than 2.1 in yet another embodiment. Polyethylene and polypropylene each have a dielectric constant (1 kHz, 23° C.) of at least 2.3 (CRC HANDBOOK OF CHEMISTRY AND PHYSICS (David R. Lide, ed. $82^d$ ed. CRC Press 2001).

In some embodiments, the NFP may have a kinematic viscosity of from 0.1 to 3000 cSt at 100° C., and from 0.5 to 1000 cSt at 100° C. in another embodiment, and from 1 to 250 cSt at 100° C. in another embodiment, and from 1 to 200 cSt at 100° C. in yet another embodiment, and from 10 to 500 cSt at 100° C. in yet another embodiment, wherein a desirable range may comprise any upper viscosity limit with any lower viscosity limit described herein.

In some embodiments any NFP described herein may have a specific gravity (ASTM D 4052, 15.6/15.6° C.) of less than 0.920 in one embodiment, and less than 0.910 in another embodiment, and from 0.650 to 0.900 in another embodiment, and from 0.700 to 0.860, and from 0.750 to 0.855 in another embodiment, and from 0.790 to 0.850 in another embodiment, and from 0.800 to 0.840 in yet another embodiment, wherein a desirable range may comprise any upper specific gravity limit with any lower specific gravity limit described herein.

In other embodiments any NFP described herein may have a boiling point of from 100° C. to 500° C. in one embodiment, and from 200° C. to 450° C. in another embodiment, and from 250° C. to 400° C. in yet another embodiment. Further, the NFP preferably has a weight average molecular weight of less than 20,000 g/mol in one embodiment, and less than 10,000 g/mol in yet another embodiment, and less than 5,000 g/mol in yet another embodiment, and less than 4,000 g/mol in yet another embodiment, and less than 2,000 g/mol in yet another embodiment, and less than 500 g/mol in yet another embodiment, and greater than 100 g/mol in yet another embodiment, wherein a desirable molecular weight range can be any combination of any upper molecular weight limit with any lower molecular weight limit described herein.

In another embodiment the NFP comprises a Group III hydrocarbon basestock. Preferably the NFP comprises a mineral oil having a saturates levels of 90% or more, preferably 92% or more, preferably 94% or more, preferably 96% or more, preferably 98% or more, preferably 99% or more, and sulfur contents less than 0.03%, preferably between 0.001 and 0.01% and VI is in excess of 120, preferably 130 or more.

Preferred NFP's of this invention are characterized in that, when blended with the polyolefin to form a plasticized composition, the NFP is miscible with the polyolefin as indicated by no change in the number of peaks in the Dynamic Mechanical Thermal Analysis (DMTA) trace as in the unplasticized polyolefin DMTA trace. Lack of miscibility is indicated by an increase in the number of peaks in DMTA trace over those in the unplasticized polyolefin. The trace is the plot of tan-delta versus temperature, as described below.

Preferred compositions of the present invention can be characterized in that the glass transition temperature ($T_g$) of the composition decreases by at least 2° C. for every 4 wt % of NFP present in the composition in one embodiment; and decreases by at least 3° C. for every 4 wt % of NFP present in the composition in another embodiment; and decreases from at least 4 to 10° C. for every 4 wt % of NFP present in the composition in yet another embodiment, while the peak melting and crystallization temperatures of the polyolefin remain constant (within 1 to 2° C.). For purpose of this invention and the claims thereto when glass transition temperature is referred to it is the peak temperature in the DMTA trace, as described below.

Preferred compositions of the present invention can be characterized in that the glass transition temperature ($T_g$) of the composition decreases by at least 2° C. for every 1 wt % of NFP present in the composition in one embodiment; preferably by at least 3° C., preferably by at least 4° C., preferably by at least 5° C., preferably by at least 6° C., preferably by at least 7° C., preferably by at least 8° C., preferably by at least 9° C., preferably by at least 10° C., preferably by at least 11° C.; preferably while the peak melting and or crystallization temperatures of the neat polyolefin remain within 1 to 5° C. of the plasticized polyolefin, preferably within 1 to 4° C., preferably within 1 to 3° C., preferably within 1 to 2° C.

Preferred compositions of the present invention can be characterized in that the glass transition temperature ($T_g$) of the plasticized composition is at least 2° C. lower than that of the neat polyolefin, preferably at least 4° C. lower, preferably at least 6° C. lower, preferably at least 8° C. lower, preferably at least 10° C. lower, preferably at least 15° C. lower, preferably at least 20° C. lower, preferably at least 25° C. lower, preferably at least 30° C. lower, preferably at least 35° C. lower, preferably at least 40° C. lower, preferably at least 45° C. lower.

Preferred compositions of the present invention can be characterized in that the plasticized composition decreases less than 3%, preferably less than 2%, preferably less than 1% in weight when stored at 70° C. for 311 hours in a dry oven as determined by ASTM D1203 using a 0.25 mm thick sheet.

Polyolefin

The NFP's described herein are blended with at least one polyolefin to prepare the plasticized compositions of this invention. Preferred polyolefins include propylene polymers and butene polymers.

In one aspect of the invention, the polyolefin is selected from polypropylene homopolymer, polypropylene copolymers, and blends thereof. The homopolymer may be atactic polypropylene, isotactic polypropylene, syndiotactic polypropylene and blends thereof. The copolymer can be a random copolymer, a statistical copolymer, a block copolymer, and blends thereof. In particular, the inventive polymer blends described herein include impact copolymers, elastomers and plastomers, any of which may be physical blends or in situ blends with the polypropylene and or polybutene. The method of making the polypropylene or polybutene is not critical, as it can be made by slurry, solution, gas phase or other suitable processes, and by using catalyst systems appropriate for the polymerization of polyolefins, such as Ziegler-Natta-type catalysts, metallocene-type catalysts, other appropriate catalyst systems or combinations thereof. In a preferred embodiment the propylene polymers and or the butene polymers are made by the catalysts, activators and processes described in U.S. Pat. No. 6,342,566, U.S. Pat. No. 6,384,142, WO 03/040201, WO 97/19991 and U.S. Pat. No. 5,741,563. Likewise the impact copolymers may be prepared by the process described in U.S. Pat. No. 6,342,566, U.S. Pat. No. 6,384,142. Such catalysts are well known in the art, and are described in, for example, ZIEGLER CATALYSTS (Gerhard Fink, Rolf Mülhaupt and Hans H. Brintzinger, eds., Springer-Verlag 1995); Resconi et al., *Selectivity in Propene Polymerization with Metallocene Catalysts,* 100 CHEM. REV. 1253-1345 (2000); and I, II METALLOCENE-BASED POLYOLEFINS (Wiley & Sons 2000).

Preferred propylene homopolymers and copolymers useful in this invention typically have:

1. an $M_w$ of 30,000 to 2,000,000 g/mol preferably 50,000 to 1,000,000, more preferably 90,000 to 500,000, as measured by GPC as described below in the test methods; and/or
2. an $M_w/M_n$ of 1 to 40, preferably 1.6 to 20, more preferably 1.8 to 10, more preferably 1.8 to 3 as measured by GPC as described below in the test methods; and/or
3. a $T_m$ (second melt) of 30 to 200° C., preferably 30 to 185° C., preferably 50 to 175, more preferably 60 to 170 as measured by the DSC method described below in the test methods; and/or
4. a crystallinity of 5 to 80%, preferably 10 to 70, more preferably 20 to 60% as measured by the DSC method described below in the test methods; and/or
5. a glass transition temperature ($T_g$) of −40° C. to 20° C., preferably −20° C. to 10° C., more preferably −10° C. to 5° C. as measured by the DMTA method described below in the test methods; and or
6. a heat of fusion (Hf) of 180 J/g or less, preferably 20 to 150 J/g, more preferably 40 to 120 J/g as measured by the DSC method described below in the test methods; and or
7. a peak crystallization temperature ($T_c$) of 15 to 120° C., preferably 20 to 115° C., more preferably 25 to 110° C., preferably 60 to 145° C., as measured by the method described below in the test methods; and or
8. a heat deflection temperature of 45 to 140° C., preferably 60 to 135° C., more preferably 75 to 125° C. as measured by the method described below in the test methods; and or
9. A Rockwell hardness (R scale) of 25 or more, preferably 40 or more, preferably 60 or more, preferably 80 or more, preferably 100 or more, preferably from 25 to 125; and or
10. a percent crystallinity of at least 30%, preferably at least 40%, alternatively at least 50%, as determined by the DSC method described below in the test methods; and or
11. a percent amorphous content of at least 50%, alternatively at least 60%, alternatively at least 70%, even alternatively between 50 and 95%, or 70% or less, preferably 60% or less, preferably 50% or less as determined by subtracting the percent crystallinity from 100, and or
12. A branching index (g') of 0.2 to 2.0, preferably 0.5 to 1.5, preferably 0.7 to 1.1, as measured by the method described below.

The polyolefin may be a propylene homopolymer. In one embodiment the propylene homopolymer has a molecular weight distribution ($M_w/M_n$) of up to 40, preferably ranging from 1.5 to 10, and from 1.8 to 7 in another embodiment, and from 1.9 to 5 in yet another embodiment, and from 2.0 to 4 in yet another embodiment. In another embodiment the propylene homopolymer has a Gardner impact strength, tested on 0.125 inch disk at 23° C., that may range from 20 in-lb to 1000 in-lb in one embodiment, and from 30 in-lb to 500 in-lb in another embodiment, and from 40 in-lb to 400 in-lb in yet another embodiment. In yet another embodiment, the 1% secant flexural modulus may range from 100 MPa to 2300 MPa, and from 200 MPa to 2100 MPa in another embodiment, and from 300 MPa to 2000 MPa in yet another embodiment, wherein a desirable polyolefin may exhibit any combination of any upper flexural modulus limit with any lower flexural modulus limit. The melt flow rate (MFR-ASTM D 1238, 230° C., 2.16 kg) of preferred propylene polymers range from 0.1 dg/min to 2500 dg/min in one embodiment, and from 0.3 to 500 dg/min in another embodiment.

The polypropylene homopolymer or propylene copolymer useful in the present invention may have some level of isotacticity. Thus, in one embodiment, a polyolefin comprising isotactic polypropylene is a useful polymer in the invention of this patent, and similarly, highly isotactic polypropylene is useful in another embodiment. As used herein, "isotactic" is defined as having at least 10% isotactic pentads according to analysis by $^{13}$C-NMR as described in the test methods below. As used herein, "highly isotactic" is defined as having at least 60% isotactic pentads according to analysis by $^{13}$C-NMR. In a desirable embodiment, a polypropylene homopolymer having at least 85% isotacticity is the polyolefin, and at least 90% isotacticity in yet another embodiment.

In another desirable embodiment, a polypropylene homopolymer having at least 85% syndiotacticity is the polyolefin, and at least 90% syndiotacticity in yet another embodiment. As used herein, "syndiotactic" is defined as having at least 10% syndiotactic pentads according to analysis by $^{13}$C-NMR as described in the test methods below. As used herein, "highly syndiotactic" is defined as having at least 60% syndiotactic pentads according to analysis by $^{13}$C-NMR.

In another embodiment the propylene homoplymer may be isotactic, highly isotactic, syndiotactic, highly syndiotactic or atactic. Atactic polypropylene is defined to be less than 10% isotactic or syndiotactic pentads. Preferred atactic polypropylenes typically have an $M_w$ of 20,000 up to 1,000, 000.

Preferred propylene polymers that are useful in this invention include those sold under the tradenames ACHIEVE™ and ESCORENE™ by ExxonMobil Chemical Company in Houston Tex.

In another embodiment of the invention, the polyolefin is a propylene copolymer, either random, or block, of propylene derived units and units selected from ethylene and $C_4$ to $C_{20}$ α-olefin derived units, typically from ethylene and $C_4$ to $C_{10}$ α-olefin derived units in another embodiment. The ethylene or $C_4$ to $C_{20}$ α-olefin derived units are present from 0.1 wt % to 50 wt % of the copolymer in one embodiment, and from 0.5 to 30 wt % in another embodiment, and from 1 to 15 wt % in yet another embodiment, and from 0.1 to 5 wt % in yet another embodiment, wherein a desirable copolymer comprises ethylene and $C_4$ to $C_{20}$ α-olefin derived units in any combination of any upper wt % limit with any lower wt % limit described herein. The propylene copolymer will have a weight average molecular weight of from greater than 8,000 g/mol in one embodiment, and greater than 10,000 g/mol in another embodiment, and greater than 12,000 g/mol in yet another embodiment, and greater than 20,000 g/mol in yet another embodiment, and less than 1,000,000 g/mol in yet another embodiment, and less than 800,000 in yet another embodiment, wherein a desirable copolymer may comprise any upper molecular weight limit with any lower molecular weight limit described herein.

Particularly desirable propylene copolymers have a molecular weight distribution ($M_w/M_n$) ranging from 1.5 to 10, and from 1.6 to 7 in another embodiment, and from 1.7 to 5 in yet another embodiment, and from 1.8 to 4 in yet another embodiment. The Gardner impact strength, tested on 0.125 inch disk at 23° C., of the propylene copolymer may range from 20 in-lb to 1000 in-lb in one embodiment, and from 30 in-lb to 500 in-lb in another embodiment, and from 40 in-lb to 400 in-lb in yet another embodiment. In yet another embodiment, the 1% secant flexural modulus of the propylene copolymer ranges from 100 MPa to 2300 MPa, and from 200 MPa to 2100 MPa in another embodiment, and from 300 MPa to 2000 MPa in yet another embodiment, wherein a desirable polyolefin may exhibit any combination of any upper flexural modulus limit with any lower flexural modulus limit. The melt flow rate (MFR) of propylene copolymer ranges from 0.1 dg/min to 2500 dg/min in one embodiment, and from 0.3 to 500 dg/min in another embodiment.

In another embodiment the polyolefin may be a propylene copolymer comprising propylene and one or more other monomers selected from the group consisting of ethylene and $C_4$ to $C_{20}$ linear, branched or cyclic monomers, and in some embodiments is a $C_4$ to $C_{12}$ linear or branched alpha-olefin, preferably butene, pentene, hexene, heptene, octene, nonene, decene, dodecene, 4-methyl-pentene-1,3-methyl pentene-1, 3,5,5-trimethyl-hexene-1, and the like. The monomers may be present at up to 50 weight %, preferably from 0 to 40 weight %, more preferably from 0.5 to 30 weight %, more preferably from 2 to 30 weight %, more preferably from 5 to 20 weight %.

In a preferred embodiment the butene homopolymers and copolymers useful in this invention typically have:
1. an $M_w$ of 30,000 to 2,000,000 g/mol preferably 50,000 to 1,000,000, more preferably 90,000 to 500,000, as measured by GPC as described below in the test methods; and/or
2. an $M_w/M_n$ of 1 to 40, preferably 1.6 to 20, more preferably 1.8 to 10, more preferably 1.8 to 3 as measured by GPC as described below in the test methods; and/or
3. a $T_m$ (second melt) of 30 to 150° C., preferably 30 to 145° C., preferably 50 to 135, as measured by the DSC method described below in the test methods; and/or
4. a crystallinity of 5 to 80%, preferably 10 to 70, more preferably 20 to 60% as determined by the DSC method described below in the test methods; and/or
5. a glass transition temperature ($T_g$) of −50° C. to 0° C. as measured by the DMTA method described below in the test methods; and or
6. a heat of fusion of 180 J/g or less, preferably 20 to 150 J/g, more preferably 40 to 120 J/g as measured by the DSC method described below in the test methods; and or
7. a peak crystallization temperature ($T_c$) of 10 to 130° C., preferably 20 to 115° C., more preferably 25 to 110° C., preferably 60 to 145° C., as measured by the method described below in the test methods; and or
8. a percent amorphous content of at least 50%, alternatively at least 60%, alternatively at least 70%, even alternatively between 50 and 95%, or 70% or less, preferably 60% or less, preferably 50% or less as determined by subtracting the percent crystallinity from 100, and or
9. A branching index (g') of 0.2 to 2.0, preferably 0.5 to 1.5, preferably 0.7 to 1.1, as measured by the method described below.

Preferred linear alpha-olefins useful as comonomers for the propylene copolymers useful in this invention include $C_3$ to $C_8$ alpha-olefins, more preferably 1-butene, 1-hexene, and 1-octene, even more preferably 1-butene. Preferred linear alpha-olefins useful as comonomers for the butene copolymers useful in this invention include $C_3$ to $C_8$ alpha-olefins, more preferably propylene, 1-hexene, and 1-octene, even more preferably propylene. Preferred branched alpha-olefins include 4-methyl-1-pentene, 3-methyl-1-pentene, and 3,5,5-trimethyl-1-hexene, 5-ethyl-1-nonene. Preferred aromatic-group-containing monomers contain up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, paramethyl styrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane and the like.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes ($M_w$ less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In a preferred embodiment one or more dienes are present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

In yet another embodiment, the Gardner impact strength, tested on 0.125 inch disk at 23° C., of the butene copolymer ranges from 20 in-lb to 1000 in-lb, and from 30 in-lb to 500 in-lb in another embodiment, and from 40 in-lb to 400 in-lb in yet another embodiment. Further, the butene copolymer may possess a 1% secant flexural modulus ranging from 100 MPa to 2300 MPa, and from 200 MPa to 2100 MPa in another embodiment, and from 300 MPa to 2000 MPa in yet another embodiment, wherein a desirable polyolefin may exhibit any combination of any upper flexural modulus limit with any lower flexural modulus limit. The melt flow rate (MFR) of desirable copolymers ranges from 0.1 dg/min to 2500 dg/min in one embodiment, and from 0.1 to 500 dg/min in another embodiment.

In another embodiment the propylene copolymer is a random copolymer, also known as an "RCP," comprising propylene and up to 20 mole % of ethylene or a $C_4$ to $C_{20}$ olefin, preferably up to 20 mole % ethylene. In particularly preferred embodiments the propylene polymer used herein is a random copolymer of propylene and ethylene, where the ethylene is present at up to 15 weight % (based upon the weight of the copolymer), preferably at 1 to 10%, more preferably 1.5 to 5 weight %, more preferably 2 to 4 weight %.

In another particularly preferred embodiments the propylene polymer used herein is a random copolymer of propylene and ethylene, where the ethylene is present at up to 15 weight % (based upon the weight of the copolymer), preferably at 1 to 10%, more preferably 1.5 to 5 weight %, more preferably 2 to 4 weight % and the polymer has a melt flow rate (MFR) in the range from 0.1 dg/min to 2500 dg/min, preferably from 0.2 to 500 dg/min, preferably from 0.3 to 200 dg/min, preferably from 1 to 100 dg/min, preferably from 5 to 50 dg/min.

In another embodiment, the polyolefin may be an impact copolymer (ICP) or block copolymer. Propylene impact copolymers are commonly used in a variety of applications where strength and impact resistance are desired such as molded and extruded automobile parts, household appliances, luggage and furniture. Propylene homopolymers alone are often unsuitable for such applications because they are too brittle and have low impact resistance particularly at low temperature, whereas propylene impact copolymers are specifically engineered for applications such as these.

A typical propylene impact copolymer contains at least two phases or components, e.g., a homopolymer component and a copolymer component. The impact copolymer may also comprise three phases such as a PP/EP/PE combination with the PP continuous and a dispersed phase with EP outside and PE inside the dispersed phase particles. These components are usually produced in a sequential polymerization process wherein the homopolymer produced in a first reactor is transferred to a second reactor where copolymer is produced and incorporated within the matrix of the homopolymer component. The copolymer component has rubbery characteristics and provides the desired impact resistance, whereas the homopolymer component provides overall stiffness.

Another important feature of ICP's is the amount of amorphous polypropylene they contain. The ICP's of this invention are characterized as having low amorphous polypropylene, preferably less than 3% by weight, more preferably less than 2% by weight, even more preferably less than 1% by weight and most preferably there is no measurable amorphous polypropylene. Percent amorphous polypropylene is determined by the method described below in the test methods.

Preferred impact copolymers may be a reactor blend (in situ blend) or a post reactor (ex-situ) blend. In one embodiment, a suitable impact copolymer comprises from 40% to 95% by weight Component A and from 5% to 60% by weight Component B based on the total weight of the impact copolymer; wherein Component A comprises propylene homopolymer or copolymer, the copolymer comprising 10% or less by weight ethylene, butene, hexene or octene comonomer; and wherein Component B comprises propylene copolymer, wherein the copolymer comprises from 5% to 70% by weight ethylene, butene, hexene and/or octene comonomer, and from about 95% to about 30% by weight propylene. In one embodiment of the impact copolymer, Component B consists essentially of propylene and from about 30% to about 65% by weight ethylene. In another embodiment, Component B comprises ethylene-propylene copolymers, ethylene-propylene-diene terpolymers, ethylene-acrylate copolymers, ethylene-vinyl acetate, styrene-butadiene copolymers, ethylene-acrylic ester copolymers, polybutadiene, polyisoprene, natural rubber, isobutylene, hydrocarbon resin (the hydrocarbon resin being characterized by a molecular weight less than 5000, a $T_g$ of about 50 to 100° C. and a softening point, Ring and Ball, as measured by ASTM E-28, of less than about 140° C.), rosin ester, and mixtures thereof. In another embodiment, Component B has a molecular weight distribution of less than 3.5. In yet another embodiment, Component B has a weight average molecular weight of at least 20,000. A useful impact copolymer is disclosed in, for example, U.S. Pat. No. 6,342,566 and U.S. Pat. No. 6,384,142.

Component B is most preferably a copolymer consisting essentially of propylene and ethylene although other propylene copolymers, ethylene copolymers or terpolymers may be suitable depending on the particular product properties desired. For example, propylene/butene, hexene or octene copolymers, and ethylene/butene, hexene or octene copolymers may be used, and propylene/ethylene/hexene-1 terpolymers may be used. In a preferred embodiment though, Component B is a copolymer comprising at least 40% by weight propylene, more preferably from about 80% by weight to about 30% by weight propylene, even more preferably from about 70% by weight to about 35% by weight propylene. The comonomer content of Component B is preferably in the range of from about 20% to about 70% by weight comonomer, more preferably from about 30% to about 65% by weight comonomer, even more preferably from about 35% to about 60% by weight comonomer. Most preferably Component B consists essentially of propylene and from about 20% to about 70% ethylene, more preferably from about 30% to about 65% ethylene, and most preferably from about 35% to about 60% ethylene.

For other Component B copolymers, the comonomer contents will need to be adjusted depending on the specific properties desired. For example, for ethylene/hexene copolymers, Component B should contain at least 17% by weight hexene and at least 83% by weight ethylene.

Component B, preferably has a narrow molecular weight distribution $M_w/M_n$ ("MWD"), i.e., lower than 5.0, preferably lower than 4.0, more preferably lower than 3.5, even more preferably lower than 3.0 and most preferably 2.5 or lower. These molecular weight distributions should be obtained in the absence of visbreaking or peroxide or other post reactor treatment molecular weight tailoring. Component B preferably has a weight average molecular weight ($M_w$ as determined by GPC) of at least 100,000, preferably at least 150,000, and most preferably at least 200,000.

Component B preferably has an intrinsic viscosity greater than 1.00 dl/g, more preferably greater than 1.50 dl/g and most preferably greater than 2.00 dl/g. The term "intrinsic viscosity" or "IV" is used conventionally herein to mean the viscosity of a solution of polymer such as Component B in a given solvent at a given temperature, when the polymer composition is at infinite dilution. According to the ASTM standard test method D 1601-78, IV measurement involves a standard capillary viscosity measuring device, in which the viscosity of a series of concentrations of the polymer in the solvent at the given temperature are determined. For Component B, decalin is a suitable solvent and a typical temperature is 135° C. From the values of the viscosity of solutions of varying concentrations, the "value" at infinite dilution can be determined by extrapolation.

Component B preferably has a composition distribution breadth index (CDBI) of greater than 60%, more preferably greater than 65%, even more preferably greater than 70%, even more preferably greater than 75%, still more preferably greater than 80%, and most preferably greater than 85%. CDBI defines the compositional variation among polymer chains in terms of ethylene (or other comonomer) content of the copolymer as a whole. CDBI is defined in U.S. Pat. No. 5,382,630, which is hereby incorporate by reference, as the weight percent of the copolymer molecules having a comonomer content within 50% of the median total molar comonomer content. The CDBI of a copolymer is readily determined utilizing well known techniques for isolating individual fractions of a sample of the copolymer. One such technique is Temperature Rising Elution Fraction (TREF), as described in Wild, et al., *J. Poly. Sci., Poly. Phys. Ed.*, vol. 20, p. 441 (1982) and U.S. Pat. No. 5,008,204, which are incorporated herein by reference.

Component B of the ICP's preferably has low crystallinity, preferably less than 10% by weight of a crystalline portion, more preferably less than 5% by weight of a crystalline portion. Where there is a crystalline portion of Component B, its composition is preferably the same as or at least similar to (within 15% by weight) the remainder of Component B in terms of overall comonomer weight percent.

The preferred melt flow rate ("MFR") of these ICP's depends on the desired end use but is typically in the range of from about 0.2 dg/min to about 200 dg/min, more preferably from about 5 dg/min to about 100 dg/min. Significantly, high MFRs, i.e., higher than 50 dg/min are obtainable. The ICP preferably has a melting point (Tm) of at least 145° C., preferably at least 150° C., more preferably at least 152° C., and most preferably at least 155° C.

The ICP's comprise from about 40% to about 95% by weight Component A and from about 5% to about 60% by weight Component B, preferably from about 50% to about 95% by weight Component A and from about 5% to about 50% Component B, even more preferably from about 60% to about 90% by weight Component A and from about 10% to about 40% by weight Component B. In the most preferred embodiment, the ICP consists essentially of Components A and B. The overall comonomer (preferably ethylene) content of the total ICP is preferably in the range of from about 2% to about 30% by weight, preferably from about 5% to about 25% by weight, even more preferably from about 5% to about 20% by weight, still more preferably from about 5% to about 15% by weight comonomer.

In another embodiment a preferred impact copolymer composition is prepared by selecting Component A and Component B such that their refractive indices (as measured by ASTM D 542-00) are within 20% of each other, preferably within 15%, preferably 10, even more preferably within 5% of each other. This selection produces impact copolymers with outstanding clarity. In another embodiment a preferred impact copolymer composition is prepared by selecting a blend of Component A and an NFP and a blend of Component B and an NFP such that refractive indices of the blends (as measured by ASTM D 542-00) are within 20% of each other, preferably within 15%, preferably 10, even more preferably within 5% of each other.

In yet another embodiment, the Gardner impact strength, tested on 0.125 inch disk at −29° C., of the propylene impact copolymer ranges from 20 in-lb to 1000 in-lb, and from 30 in-lb to 500 in-lb in another embodiment, and from 40 in-lb to 400 in-lb in yet another embodiment. Further, the 1% secant flexural modulus of the propylene impact copolymer may range from 100 MPa to 2300 MPa in one embodiment, and from 200 MPa to 2100 MPa in another embodiment, and from 300 MPa to 2000 MPa in yet another embodiment, wherein a desirable polyolefin may exhibit any combination of any upper flexural modulus limit with any lower flexural modulus limit. The melt flow rate (MFR) (ASTM D 1238, 230° C., 2.16 kg) of desirable homopolymers ranges from 0.1 dg/min to 2500 dg/min in one embodiment, and from 0.3 to 500 dg/min in another embodiment.

Another suitable polyolefin comprises a blend of a polypropylene homopolymer or propylene copolymer with a plastomer. The plastomers that are useful in the present invention may be described as polyolefin copolymers having a density of from 0.85 to 0.915 g/cm$^3$ ASTM D 4703 Method B and ASTM D 1505—the first of these is compression molding at a cooling rate of 15° C./min and the second is the Gradient Density Column method for density determination and a melt index (MI) between 0.10 and 30 dg/min (ASTM D 1238; 190° C., 2.1 kg). In one embodiment, the useful plastomer is a copolymer of ethylene derived units and at least one of $C_3$ to $C_{10}$ α-olefin derived units, the copolymer having a density less than 0.915 g/cm$^3$. The amount of comonomer ($C_3$ to $C_{10}$ α-olefin derived units) present in the plastomer ranges from 2 wt % to 35 wt % in one embodiment, and from 5 wt % to 30 wt % in another embodiment, and from 15 wt % to 25 wt % in yet another embodiment, and from 20 wt % to 30 wt % in yet another embodiment.

The plastomer useful in the invention has a melt index of between 0.10 and 20 dg/min in one embodiment, and from 0.2 to 10 dg/min in another embodiment, and from 0.3 to 8 dg/min in yet another embodiment. The average molecular weight of useful plastomers ranges from 10,000 to 800,000 in one embodiment, and from 20,000 to 700,000 in another embodiment. The 1% secant flexural modulus of useful plastomers ranges from 10 MPa to 150 MPa in one embodiment, and from 20 MPa to 100 MPa in another embodiment. Further, the plastomer that is useful in compositions of the present invention has a melting temperature ($T_m$) of from 30 to 80° C. (first melt peak) and from 50 to 125° C. (second melt peak) in one embodiment, and from 40 to 70° C. (first melt peak) and from 50 to 100° C. (second melt peak) in another embodiment.

Plastomers useful in the present invention are metallocene catalyzed copolymers of ethylene derived units and higher α-olefin derived units such as propylene, 1-butene, 1-hexene and 1-octene, and which contain enough of one or more of these comonomer units to yield a density between 0.860 and 0.900 g/cm$^3$ in one embodiment. The molecular weight distribution ($M_w/M_n$) of desirable plastomers ranges from 1.5 to 5 in one embodiment, and from 2.0 to 4 in another embodiment. Examples of a commercially available plastomers are EXACT 4150, a copolymer of ethylene and 1-hexene, the 1-hexene derived units making up from 18 to 22 wt % of the plastomer and having a density of 0.895 g/cm$^3$ and MI of 3.5 dg/min (ExxonMobil Chemical Company, Houston, Tex.); and EXACT 8201, a copolymer of ethylene and 1-octene, the 1-octene derived units making up from 26 to 30 wt % of the plastomer, and having a density of 0.882 g/cm$^3$ and MI of 1.0 dg/min (ExxonMobil Chemical Company, Houston, Tex.).

In another embodiment polymers that are useful in this invention include homopolymers and random copolymers of propylene having a heat of fusion as determined by Differential Scanning Calorimetry (DSC) of less than 50 J/g, a melt index (MI) of less than 20 dg/min and or an MFR of 20 dg/min or less, and contains stereoregular propylene crystallinity preferably isotactic stereoregular propylene crystallinity. In another embodiment the polymer is a random copolymer of propylene and at least one comonomer selected from ethylene, $C_4$-$C_{12}$ α-olefins, and combinations thereof. Preferably the random copolymers of propylene comprises from 2 wt % to 25 wt % polymerized ethylene units, based on the total weight of the polymer; has a narrow composition distribution; has a melting point ($T_m$) of from 25° C. to 120° C., or from 35° C. to 80° C.; has a heat of fusion within the range having an upper limit of 50 J/g or 25 J/g and a lower limit of 1 J/g or 3 J/g; has a molecular weight distribution $M_w/M_n$ of from 1.8 to 4.5; and has a melt index (MI) of less than 20 dg/min, or less than 15 dg/min. The intermolecular composition distribution of the copolymer is determined by thermal fractionation in a solvent. A typical solvent is a saturated hydrocarbon such as hexane or heptane. The thermal fractionation procedure is described below. Typically, approximately 75% by weight, preferably 85% by weight, of the copolymer is isolated as one or two adjacent, soluble fractions with the balance of the copolymer in immediately preceding or succeeding fractions. Each of these fractions has a composition (wt % comonomer such as ethylene or other α-olefin) with a difference of no greater than 20% (relative), preferably 10% (relative), of the average weight % comonomer of the copolymer. The copolymer has a narrow composition distribution if it meets the fractionation test described above.

A particularly preferred polymer useful in the present invention is an elastic polymer with a moderate level of crystallinity due to stereoregular propylene sequences. The polymer can be: (A) a propylene homopolymer in which the stereoregularity is disrupted in some manner such as by regio-inversions; (B) a random propylene copolymer in which the propylene stereoregularity is disrupted at least in part by comonomers; or (C) a combination of (A) and (B).

In one embodiment, the polymer further includes a non-conjugated diene monomer to aid in vulcanization and other chemical modification of the blend composition. The amount of diene present in the polymer is preferably less than 10% by weight, and more preferably less than 5% by weight. The diene may be any non-conjugated diene which is commonly used for the vulcanization of ethylene propylene rubbers including, but not limited to, ethylidene norbornene, vinyl norbornene, and dicyclopentadiene.

In one embodiment, the polymer is a random copolymer of propylene and at least one comonomer selected from ethylene, $C_4$-$C_{12}$ α-olefins, and combinations thereof. In a particular aspect of this embodiment, the copolymer includes ethylene-derived units in an amount ranging from a lower limit of 1%, 2%, 5%, 6%, 8%, or 10% by weight to an upper limit of 20%, 25%, or 28% by weight. This embodiment will also include propylene-derived units present in the copolymer in an amount ranging from a lower limit of 72%, 75%, or 80% by weight to an upper limit of 99%, 98%, 95%, 94%, 92%, or 90% by weight. These percentages by weight are based on the total weight of the propylene and ethylene-derived units; i.e., based on the sum of weight percent propylene-derived units and weight percent ethylene-derived units being 100%. The ethylene composition of a polymer can be measured as follows. A thin homogeneous film is pressed at a temperature of about 150° C. or greater, then mounted on a Perkin Elmer PE 1760 infrared spectrophotometer. A full spectrum of the sample from 600 cm$^{-1}$ to 4000 cm$^{-1}$ is recorded and the monomer weight percent of ethylene can be calculated according to the following equation: Ethylene wt %=82.585-111.987X+30.045 X$^2$, wherein X is the ratio of the peak height at 1155 cm$^{-1}$ and peak height at either 722 cm$^{-1}$ or 732 cm$^{-1}$, whichever is higher. The concentrations of other monomers in the polymer can also be measured using this method.

Comonomer content of discrete molecular weight ranges can be measured by Fourier Transform Infrared Spectroscopy (FTIR) in conjunction with samples collected by GPC. One such method is described in Wheeler and Willis, Applied Spectroscopy, 1993, vol. 47, pp. 1128-1130. Different but similar methods are equally functional for this purpose and well known to those skilled in the art.

Comonomer content and sequence distribution of the polymers can be measured by $^{13}$C nuclear magnetic resonance ($^{13}$C NMR), and such method is well known to those skilled in the art.

In one embodiment, the polymer is a random propylene copolymer having a narrow composition distribution. In another embodiment, the polymer is a random propylene copolymer having a narrow composition distribution and a melting point of from 25° C. to 110° C. The copolymer is described as random because for a polymer comprising propylene, comonomer, and optionally diene, the number and distribution of comonomer residues is consistent with the random statistical polymerization of the monomers. In stereoblock structures, the number of block monomer residues of any one kind adjacent to one another is greater than predicted from a statistical distribution in random copolymers with a similar composition. Historical ethylene-propylene copolymers with stereoblock structure have a distribution of ethylene residues consistent with these blocky structures rather than a random statistical distribution of the monomer residues in the polymer. The intramolecular composition distribution (i.e., randomness) of the copolymer may be determined by $^{13}$C NMR, which locates the comonomer residues in relation to the neighbouring propylene residues. The intermolecular composition distribution of the copolymer is determined by thermal fractionation in a solvent. A typical solvent is a saturated hydrocarbon such as hexane or heptane. Typically, approximately 75% by weight, preferably 85% by weight, of the copolymer is isolated as one or two adjacent, soluble fractions with the balance of the copolymer in immediately preceding or succeeding fractions. Each of these fractions has a composition (wt % comonomer such as ethylene or other α-olefin) with a difference of no greater than 20% (relative), preferably 10% (relative), of the average weight % comonomer of the copolymer. The copolymer has a narrow composition distribution if it meets the fractionation test described above. To produce a copolymer having the desired randomness and narrow composition, it is beneficial if (1) a single sited metallocene catalyst is used which allows only a single statistical mode of addition of the first and second monomer sequences and (2) the copolymer is well-mixed in a continuous flow stirred tank polymerization reactor which allows only a single polymerization environment for substantially all of the polymer chains of the copolymer.

The crystallinity of the polymers may be expressed in terms of heat of fusion. Embodiments of the present invention include polymers having a heat of fusion, as determined by DSC, ranging from a lower limit of 1.0 J/g, or 3.0 J/g, to an upper limit of 50 J/g, or 10 J/g.

The crystallinity of the polymer may also be expressed in terms of crystallinity percent. The thermal energy for the highest order of polypropylene is estimated at 207 J/g. That is, 100% crystallinity is equal to 207 J/g. Preferably, the polymer has a polypropylene crystallinity within the range having an upper limit of 65%, 40%, 30%, 25%, or 20%, and a lower limit of 1%, 3%, 5%, 7%, or 8%.

The level of crystallinity is also reflected in the melting point. The term "melting point," as used herein, is the highest peak highest meaning the largest amount of polymer being reflected as opposed to the peak occurring at the highest temperature among principal and secondary melting peaks as determined by DSC, discussed above. In one embodiment of the present invention, the polymer has a single melting point. Typically, a sample of propylene copolymer will show secondary melting peaks adjacent to the principal peak, which are considered together as a single melting point. The highest of these peaks is considered the melting point. Preferred polymers herein preferably have a melting point by DSC ranging from an upper limit of 110° C., 105° C., 90° C., 80° C., or 70° C., to a lower limit of 0° C., 20° C., 25° C., 30° C., 35° C., 40° C., or 45° C.

Such polymers used in the invention typically have a weight average molecular weight (Mw) within the range having an upper limit of 5,000,000 g/mol, 1,000,000 g/mol, or 500,000 g/mol, and a lower limit of 10,000 g/mol, 20,000 g/mol, or 80,000 g/mol, and a molecular weight distribution Mw/Mn (MWD), sometimes referred to as a "polydispersity index" (PDI), ranging from a lower limit of 1.5, 1.8, or 2.0 to an upper limit of 40, 20, 10, 5, or 4.5. In one embodiment, the polymer has a Mooney viscosity, ML(1+4) @ 125° C., of 100 or less, 75 or less, 60 or less, or 30 or less. Mooney viscosity, as used herein, can be measured as ML(1+4) @ 125° C. according to ASTM D1646, unless otherwise specified.

In some embodiments, the polymers useful in the present invention can have a tacticity index (m/r) ranging from a lower limit of 4 or 6 to an upper limit of 8, 10, or 12. The tacticity index, expressed herein as "m/r", is determined by $^{13}C$ nuclear magnetic resonance (NMR). The tacticity index m/r is calculated as defined in H. N. Cheng, *Macromolecules*, 17, 1950 (1984). The designation "m" or "r" describes the stereochemistry of pairs of contiguous propylene groups, "m" referring to meso and "r" to racemic. An m/r ratio of 0 to less than 1.0 generally describes a syndiotactic polymer, and an m/r ratio of 1.0 an atactic material, and an m/r ratio of greater than 1.0 an isotactic material. An isotactic material theoretically may have a ratio approaching infinity, and many by-product atactic polymers have sufficient isotactic content to result in ratios of greater than 50.

In one embodiment, the polymer has isotactic stereoregular propylene crystallinity. The term "stereoregular" as used herein means that the predominant number, i.e. greater than 80%, of the propylene residues in the polypropylene or in the polypropylene continuous phase of a blend, such as impact copolymer exclusive of any other monomer such as ethylene, has the same 1.2 insertion and the stereochemical orientation of the pendant methyl groups is the same, either meso or racemic.

An ancillary procedure for the description of the tacticity of the propylene units of embodiments of the current invention is the use of triad tacticity. The triad tacticity of a polymer is the relative tacticity of a sequence of three adjacent propylene units, a chain consisting of head to tail bonds, expressed as a binary combination of m and r sequences. It is usually expressed for copolymers of the present invention as the ratio of the number of units of the specified tacticity to all of the propylene triads in the copolymer.

The triad tacticity (mm fraction) of a propylene copolymer can be determined from a $^{13}C$ NMR spectrum of the propylene copolymer and the following formula:

$$\text{mm Fraction} = \frac{PPP(mm)}{PPP(mm) + PPP(mr) + PPP(rr)}$$

where PPP(mm), PPP(mr) and PPP(rr) denote peak areas derived from the methyl groups of the second units in the following three propylene unit chains consisting of head-to-tail bonds:

PPP(mm):

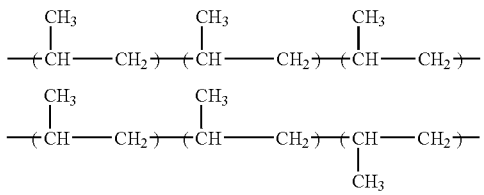

PPP(mr):

PPP(rr):

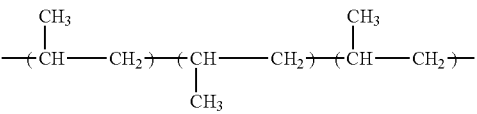

The $^{13}C$ NMR spectrum of the propylene copolymer is measured as described in U.S. Pat. No. 5,504,172. The spectrum relating to the methyl carbon region (19-23 parts per million (ppm)) can be divided into a first region (21.2-21.9 ppm), a second region (20.3-21.0 ppm) and a third region (19.5-20.3 ppm). Each peak in the spectrum was assigned with reference to an article in the journal Polymer, Volume 30 (1989), page 1350. In the first region, the methyl group of the second unit in the three propylene unit chain represented by PPP (mm) resonates. In the second region, the methyl group of the second unit in the three propylene unit chain represented by PPP (mr) resonates, and the methyl group (PPE-methyl group) of a propylene unit whose adjacent units are a propylene unit and an ethylene unit resonates (in the vicinity of 20.7 ppm). In the third region, the methyl group of the second unit in the three propylene unit chain represented by PPP (rr) resonates, and the methyl group (EPE-methyl group) of a propylene unit whose adjacent units are ethylene units resonates (in the vicinity of 19.8 ppm).

The calculation of the triad tacticity is outlined in the techniques shown in U.S. Pat. No. 5,504,172. Subtraction of the peak areas for the error in propylene insertions (both 2.1 and 1.3) from peak areas from the total peak areas of the second region and the third region, the peak areas based on the 3 propylene units-chains (PPP(mr) and PPP(rr)) consisting of head-to-tail bonds can be obtained. Thus, the peak areas of PPP(mm), PPP(mr) and PPP(rr) can be evaluated, and hence the triad tacticity of the propylene unit chain consisting of head-to-tail bonds can be determined.

Preferred polymers of embodiments of the present invention have a triad tacticity of three propylene units, as measured by $^{13}$C NMR, of 75% or greater, 80% or greater, 82% or greater, 85% or greater, or 90% or greater.

In embodiments of the present invention, the polymer preferably has a melt index (MI) of 20 dg/min or less, 7 dg/min or less, 5 dg/min or less, or 2 dg/min or less, or less than 2 dg/min. The determination of the MI of the polymer is according to ASTM D1238 (190° C., 2.16 kg). In this version of the method a portion of the sample extruded during the test was collected and weighed. This is commonly referred to as the modification 1 of the experimental procedure. The sample analysis is conducted at 190° C. with a 1 minute preheat on the sample to provide a steady temperature for the duration of the experiment.

In one embodiment, the polymer used in the present invention is described in detail as the "Second Polymer Component (SPC)" in WO 00/69963, WO 00/01766, WO 99/07788, WO 02/083753, and described in further detail as the "Propylene Olefin Copolymer" in WO 00/01745, all of which are fully incorporated by reference herein for purposes of U.S. patent practice.

Preparing the Polyolefin/NFP Blend

The polyolefin suitable for use in the present invention can be in any physical form when used to blend with the NFP of the invention. In one embodiment, reactor granules, defined as the granules of polymer that are isolated from the polymerization reactor prior to any processing procedures, are used to blend with the NFP of the invention. The reactor granules have an average diameter of from 50 µm to 10 mm in one embodiment, and from 10 µm to 5 mm in another embodiment. In another embodiment, the polyolefin is in the form of pellets, such as, for example, having an average diameter of from 1 mm to 10 mm that are formed from melt extrusion of the reactor granules.

In one embodiment of the invention, the polyolefin suitable for the composition excludes physical blends of polypropylene with other polyolefins, and in particular, excludes physical blends of polypropylene with low molecular weight (500 to 10,000 g/mol) polyethylene or polyethylene copolymers, meaning that, low molecular weight polyethylene or polyethylene copolymers are not purposefully added in any amount to the polyolefin (e.g., polypropylene homopolymer or copolymer) compositions of the invention, such as is the case in, for example, WO 01/18109 A1.

The polyolefin and NFP can be blended by any suitable means, and are typically blended to obtain a homogeneous, single phase mixture. For example, they may be blended in a tumbler, static mixer, batch mixer, extruder, or a combination thereof. The mixing step may take place as part of a processing method used to fabricate articles, such as in the extruder on an injection molding maching or fiber line.

In one embodiment of compositions of the present invention, conventional plasticizers such as is commonly used for poly(vinyl chloride) are substantially absent. In particular, plasticizers such as phthalates, adipates, trimellitate esters, polyesters, and other functionalized plasticizers as disclosed in, for example, U.S. Pat. No. 3,318,835; U.S. Pat. No. 4,409,345; WO 02/31044 A1; and PLASTICS ADDITIVES 499-504 (Geoffrey Pritchard, ed., Chapman & Hall 1998) are substantially absent. By "substantially absent", it is meant that these compounds are not added deliberately to the compositions and if present at all, are present at less than 0.5 weight %.

Oils such as naphthenic and other aromatic containing oils are preferably present to less than 0.5 wt % of the compositions of the invention in a further embodiment. Also, aromatic moieties and carbon-carbon unsaturation are substantially absent from the non-functionalized plasticizers used in the present invention in yet another embodiment. Aromatic moieties include a compound whose molecules have the ring structure characteristic of benzene, naphthalene, phenanthrene, anthracene, etc. By "substantially absent", it is meant that these aromatic compounds or moieties are not added deliberately to the compositions, and if present, are present to less than 0.5 wt % of the composition.

In another embodiment of compositions of the present invention, conventional plasticizers, elastomers, or "compatibilizers" such as low molecular weight polyethylene are substantially absent. In particular, ethylene homopolymers and copolymers having a weight average molecular weight of from 500 to 10,000 are substantially absent. Such polyethylene compatibilizers are disclosed in, for example, WO 01/18109 A1. By "substantially absent", it is meant that these compounds are not added deliberately to the compositions and, if present, are present at less than 5 weight %, more preferably less than 4 weight %, more preferably less than 3 weight %, more preferably less than 2 weight %, more preferably less than 1 weight %, more preferably less than 0.5 weight %, based upon the weight of the polyolefin, the ethylene polymer or copolymer, and the NFP.

The polyolefin compositions of the present invention may also contain other additives. Those additives include adjuvants, oils, plasticizers, block, antiblock, color masterbatches, processing aids, neutralizers, lubricants, waxes, antioxidants, nucleating agents, acid scavengers, stabilizers, surfactants, anticorrosion agents, cavitating agents, blowing agents, other UV absorbers such as chain-breaking antioxidants, etc., quenchers, antistatic agents, slip agents, pigments, dyes, fillers and cure agents such as peroxide. The additives may be present in the typically effective amounts well known in the art, such as 0.001 weight % to 10 weight %. Preferably, dyes and other colorants common in the industry may be present from 0.01 to 10 wt % in one embodiment, and from 0.1 to 6 wt % in another embodiment. Suitable nucleating agents are disclosed by, for example, H. N. Beck in *Heterogeneous Nucleating Agents for Polypropylene Crystallization*, 11 J. APPLIED POLY. SCI. 673-685 (1967) and in *Heterogeneous Nucleation Studies on Polypropylene*, 21 J. POLY. SCI.: POLY. LETTERS 347-351 (1983). Examples of suitable nucleating agents are sodium benzoate, sodium 2,2'-methylenebis(4, 6-di-tert-butylphenyl) phosphate, aluminum 2,2'-methylenebis(4,6-di-tert-butylphenyl) phosphate, dibenzylidene sorbitol, di(p-tolylidene) sorbitol, di(p-ethylbenzylidene) sorbitol, bis(3,4-dimethylbenzylidene) sorbitol, and N',N'-dicyclohexyl-2,6-naphthalenedicarboxamide, and salts of disproportionated rosin esters. The foregoing list is intended to be illustrative of suitable choices of nucleating agents for inclusion in the instant formulations.

In particular, antioxidants and stabilizers such as organic phosphites, hindered amines, and phenolic antioxidants may be present in the polyolefin compositions of the invention from 0.001 to 2 wt % in one embodiment, and from 0.01 to 0.8 wt % in another embodiment, and from 0.02 to 0.5 wt % in yet another embodiment. Non-limiting examples of organic phosphites that are suitable are tris(2,4-di-tert-butylphenyl) phosphite (IRGAFOS 168) and di(2,4-di-tert-butylphenyl)

pentaerithritol diphosphite (ULTRANOX 626). Non-limiting examples of hindered amines include poly[2-N,N'-di(2,2,6, 6-tetramethyl-4-piperidinyl)-hexanediamine-4-(1-amino-1, 1,3,3-tetramethylbutane)sym-triazine] (CHIMASORB 944); bis(1,2,2,6,6-pentamethyl-4-piperidyl)sebacate (TINUVIN 770). Non-limiting examples of phenolic antioxidants include pentaerythrityl tetrakis(3,5-di-tert-butyl-4-hydroxyphenyl) propionate (IRGANOX 1010); and 1,3,5-Tri(3,5-di-tert-butyl-4-hydroxybenzyl-isocyanurate (IRGANOX 3114). Preferred antioxidants include phenolic antioxidants, such as Irganox 1010, Irganox, 1076 both available from Ciba-Geigy.

Preferred oils include paraffinic or napthenic oils such as Primol 352, or Primol 876 available from ExxonMobil Chemical France, S.A. in Paris, France. More preferred oils include aliphatic napthenic oils, white oils or the like.

Fillers may be present from 0.1 to 50 wt % in one embodiment, and from 0.1 to 25 wt % of the composition in another embodiment, and from 0.2 to 10 wt % in yet another embodiment. Desirable fillers include but not limited to titanium dioxide, silicon carbide, silica (and other oxides of silica, precipitated or not), antimony oxide, lead carbonate, zinc white, lithopone, zircon, corundum, spinel, apatite, Barytes powder, barium sulfate, magnesiter, carbon black, dolomite, calcium carbonate, talc and hydrotalcite compounds of the ions Mg, Ca, or Zn with Al, Cr or Fe and $CO_3$ and/or $HPO_4$, hydrated or not; quartz powder, hydrochloric magnesium carbonate, glass fibers, clays, alumina, and other metal oxides and carbonates, metal hydroxides, chrome, phosphorous and brominated flame retardants, antimony trioxide, silica, silicone, and blends thereof. These fillers may particularly include any other fillers and porous fillers and supports known in the art, and may have the NFP of the invention pre-contacted, or pre-absorbed into the filler prior to addition to the polyolefin in one embodiment.

Preferred fillers, cavitating agents and/or nucleating agents include titanium dioxide, calcium carbonate, barium sulfate, silica, silicon dioxide, carbon black, sand, glass beads, mineral aggregates, talc, clay and the like.

More particularly, in one embodiment of the present invention, the NFP, or some portion of the NFP, may be blended with a filler, desirably a porous filler. The NFP and filler may be blended by, for example, a tumbler or other wet blending apparatus. The NFP and filler in this embodiment are blended for a time suitable to form a homogenous composition of NFP and filler, desirably from 1 minute to 5 hours in one embodiment. This NFP/filler blend may then be blended with the polyolefin useful in the invention in order to effectuate plastication of the polyolefin. In another embodiment, a porous filler may be contacted with the NFP, or some portion thereof, prior to contacting the filler with the polyolefin. In another embodiment, the porous filler, polyolefin and NFP are contacted simultaneously (or in the same blending apparatus). In any case, the NFP may be present from 0.1 to 60 wt % of the composition, and from 0.2 to 40 wt % in another embodiment, and from 0.3 to 20 wt % in yet another embodiment.

Fatty acid salts may also be present in the polyolefin compositions of the present invention. Such salts may be present from 0.001 to 1 wt % of the composition in one embodiment, and from 0.01 to 0.8 wt % in another embodiment. Examples of fatty acid metal salts include lauric acid, stearic acid, succinic acid, stearyl lactic acid, lactic acid, phthalic acid, benzoic acid, hydroxystearic acid, ricinoleic acid, naphthenic acid, oleic acid, palmitic acid, and erucic acid, suitable metals including Li, Na, Mg, Ca, Sr, Ba, Zn, Cd, Al, Sn, Pb and so forth. Preferable fatty acid salts are selected from magnesium stearate, calcium stearate, sodium stearate, zinc stearate, calcium oleate, zinc oleate, and magnesium oleate.

In some embodiments the plasticized polyolefins produced by this invention may be blended with one or more other polymers, including but not limited to, thermoplastic polymer(s) and/or elastomer(s).

By "thermoplastic polymer(s)" is meant a polymer that can be melted by heat and then cooled with out appreciable change in properties. Thermoplastic polymers typically include, but are not limited to, polyolefins, polyamides, polyesters, polycarbonates, polysulfones, polyacetals, polylactones, acrylonitrile-butadiene-styrene resins, polyphenylene oxide, polyphenylene sulfide, styrene-acrylonitrile resins, styrene maleic anhydride, polyimides, aromatic polyketones, or mixtures of two or more of the above. Preferred polyolefins include, but are not limited to, polymers comprising one or more linear, branched or cyclic $C_2$ to $C_{40}$ olefins, preferably polymers comprising propylene copolymerized with one or more $C_3$ to $C_{40}$ olefins, preferably a $C_3$ to $C_{20}$ alpha olefin, more preferably $C_3$ to $C_{10}$ alpha-olefins. More preferred polyolefins include, but are not limited to, polymers comprising ethylene including but not limited to ethylene copolymerized with a $C_3$ to $C_{40}$ olefin, preferably a $C_3$ to $C_{20}$ alpha olefin, more preferably propylene and or butene.

By elastomers is meant all natural and synthetic rubbers, including those defined in ASTM D1566. Examples of preferred elastomers include, but are not limited to, ethylene propylene rubber, ethylene propylene diene monomer rubber, styrenic block copolymer rubbers (including SI, SIS, SB, SBS, SIBS and the like, where S=styrene, I=isobutylene, and B=butadiene), butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, polybutadiene rubber (both cis and trans).

In another embodiment, the blend comprising the NFP may further be combined with one or more of polybutene, ethylene vinyl acetate, low density polyethylene (density 0.915 to less than 0.935 g/cm³) linear low density polyethylene, ultra low density polyethylene (density 0.86 to less than 0.90 g/cm³), very low density polyethylene (density 0.90 to less than 0.915 g/cm³), medium density polyethylene (density 0.935 to less than 0.945 g/cm³), high density polyethylene (density 0.945 to 0.98 g/cm³), ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, crosslinked polyethylene, copolymers of ethylene and vinyl alcohol (EVOH), polymers of aromatic monomers such as polystyrene, poly-1 esters, polyacetal, polyvinylidine fluoride, polyethylene glycols and/or polyisobutylene. Preferred polymers include those available from Exxon Chemical Company in Baytown, Tex. under the tradenames EXCEED™ and EXACT™.

In another embodiment, tackifiers may be blended with the plasticized polyolefins of this invention. Examples of useful tackifiers include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, and hydrogenated rosin esters. In some embodiments the tackifier is hydrogenated. In other embodiments the tackifier is non-polar. (Non-polar meaning that the tackifier is substantially free of monomers having polar groups. Preferably the polar groups are not present, however if they are preferably they are not present at more that 5 weight %, preferably not more that 2 weight %, even more preferably no more than 0.5 weight %.) In some embodiments the tackifier has a softening point (Ring and Ball, as measured by ASTM E-28) of 80° C. to 140° C., preferably 100° C. to 130° C. The tackifier, if present, is typically present at about 1 weight % to about 50 weight %, based upon the weight of the blend, more preferably 10 weight % to 40 weight %, even more preferably 20 weight % to 40 weight %. Preferably however, tackifier is not present, or if present, is present at less than 10 weight %, preferably less than 5 weight %, more preferably at less than 1 weight %.

More particularly, the components of the polyolefinic composition of the present invention may be blended by any suitable means to form the plasticized polyolefin, which is then suitable for further processing into useful articles. In one aspect of the invention, the polyolefin and NFP are blended, or melt blended, in an apparatus such as an extruder or batch mixer. The polyolefin may also be blended with the NFP using a tumbler, double-cone blender, ribbon blender, or other suitable blender. In yet another embodiment, the polyolefin and NFP are blended by a combination of, for example, a tumbler, followed by melt blending in an extruder. Extrusion technology for polypropylene is described in more detail in, for example, PLASTICS EXTRUSION TECHNOLOGY 26-37 (Friedhelm Hensen, ed. Hanser Publishers 1988) and in POLYPROPYLENE HANDBOOK 304-348 (Edward P. Moore, Jr. ed., Hanser Publishers 1996).

More particularly, the components of the polyolefinic composition of the present invention may be blended in solution by any suitable means to form the plasticized polyolefin, by using a solvent that dissolves both components to a significant extent. The blending may occur at any temperature or pressure where the NFP and the polyolefin remain in solution. Preferred conditions include blending at high temperatures, such as 20° C. or more, preferably 40° C. or more over the melting point of the polyolefin. For example iPP would typically be solution blended with the NFP at a temperature of 200° C. or more, preferably 220° C. or more. Such solution blending would be particularly useful in processes where the polyolefin is made by solution process and the NFP is added directly to the finishing train, rather than added to the dry polymer in another blending step altogether. Such solution blending would also be particularly useful in processes where the polyolefin is made in a bulk or high pressure process where the both the polymer and the NFP were soluble in the monomer. As with the solution process the NFP is added directly to the finishing train, rather than added to the dry polymer in another blending step altogether.

The polyolefin suitable for use in the present invention can be in any physical form when used to blend with the NFP of the invention. In one embodiment, reactor granules, defined as the granules of polymer that are isolated from the polymerization reactor, are used to blend with the NFP of the invention. The reactor granules have an average diameter of from 10 μm to 5 mm, and from 50 μm to 10 mm in another embodiment. Alternately, the polyolefin is in the form of pellets, such as, for example, having an average diameter of from 1 mm to 6 mm that are formed from melt extrusion of the reactor granules.

One method of blending the NFP with the polyolefin is to contact the components in a tumbler, the polyolefin being in the form of reactor granules. This works particularly well with polypropylene homopolymer and random copolymer. This can then be followed, if desired, by melt blending in an extruder. Another method of blending the components is to melt blend the polyolefin pellets with the NFP directly in an extruder or Brabender.

Thus, in the cases of injection molding of various articles, simple solid state blends of the pellets serve equally as well as pelletized melt state blends of raw polymer granules, of granules with pellets, or of pellets of the two components since the forming process includes a remelting and mixing of the raw material. In the process of compression molding of medical devices, however, little mixing of the melt components occurs, and a pelletized melt blend would be preferred over simple solid state blends of the constituent pellets and/or granules. Those skilled in the art will be able to determine the appropriate procedure for blending of the polymers to balance the need for intimate mixing of the component ingredients with the desire for process economy.

Applications

The resultant plasticized polyolefin of the present invention may be processed by any suitable means such as by calendering, casting, coating, compounding, extrusion, foamed, laminated, blow molding, compression molding, injection molding, thermoforming, transfer molding, cast molding, rotational molding, casting such as for films, spun or melt bonded such as for fibers, or other forms of processing such as described in, for example, PLASTICS PROCESSING (Radian Corporation, Noyes Data Corp. 1986). More particularly, with respect to the physical process of producing the blend, sufficient mixing should take place to assure that a uniform blend will be produced prior to conversion into a finished product.

The compositions of this invention (and blends thereof as described above) may be used in any known thermoplastic or elastomer application. Examples include uses in molded parts, films, tapes, sheets, tubing, hose, sheeting, wire and cable coating, adhesives, shoesoles, bumpers, gaskets, bellows, films, fibers, elastic fibers, nonwovens, spunbonds, sealants, surgical gowns and medical devices.

These devices may be made or formed by any useful forming means for forming polyolefins. This will include, at least, molding including compression molding, injection molding, blow molding, and transfer molding; film blowing or casting; extrusion, and thermoforming; as well as by lamination, pultrusion, protrusion, draw reduction, rotational molding, spinbonding, melt spinning, melt blowing; or combinations thereof. Use of at least thermoforming or film applications allows for the possibility of and derivation of benefits from uniaxial or biaxial orientation of the radiation tolerant material.

Adhesives

The polymers of this invention or blends thereof can be used as radiation resistant adhesives, either alone or combined with tackifiers. Preferred tackifiers are described above. The tackifier is typically present at about 1 weight % to about 50 weight %, based upon the weight of the blend, more preferably 10 weight % to 40 weight %, even more preferably 20 weight % to 40 weight %. Other additives, as described above, may be added also.

The radiation resistant adhesives of this invention can be used in any adhesive application, including but not limited to, disposables, packaging, laminates, pressure sensitive adhesives, tapes labels, wood binding, paper binding, non-wovens, road marking, reflective coatings, and the like. In a preferred embodiment the adhesives of this invention can be used for disposable diaper and napkin chassis construction, elastic attachment in disposable goods converting, packaging, labeling, bookbinding, woodworking, and other assembly applications. Particularly preferred applications include: baby diaper leg elastic, diaper frontal tape, diaper standing leg cuff, diaper chassis construction, diaper core stabilization, diaper liquid transfer layer, diaper outer cover lamination, diaper elastic cuff lamination, feminine napkin core stabilization, feminine napkin adhesive strip, industrial filtration bonding, industrial filter material lamination, filter mask lamination, surgical gown lamination, surgical drape lamination, and perishable products packaging.

Films

The compositions described above and the blends thereof may be formed into monolayer or multilayer films. These films may be formed by any of the conventional techniques known in the art including extrusion, co-extrusion, extrusion coating, lamination, blowing and casting. The film may be obtained by the flat film or tubular process which may be followed by orientation in an uniaxial direction or in two mutually perpendicular directions in the plane of the film. One or more of the layers of the film may be oriented in the transverse and/or longitudinal directions to the same or different extents. This orientation may occur before or after the individual layers are brought together. For example a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15 preferably 7 to 9. However in another embodiment the film is oriented to the same extent in both the MD and TD directions.

In another embodiment the layer comprising the plasticized polyolefin composition of this invention (and/or blends thereof) may be combined with one or more other layers. The other layer(s) may be any layer typically included in multilayer film structures. For example the other layer or layers may be:

1. Polyolefins

Preferred polyolefins include homopolymers or copolymers of C2 to C40 olefins, preferably C2 to C20 olefins, preferably a copolymer of an alpha-olefin and another olefin or alpha-olefin (ethylene is defined to be an alpha-olefin for purposes of this invention). Preferably homopolyethylene, homopolypropylene, propylene copolymerized with ethylene and or butene, ethylene copolymerized with one or more of propylene, butene or hexene, and optional dienes. Preferred examples include thermoplastic polymers such as ultra low density polyethylene, very low density polyethylene, linear low density polyethylene, low density polyethylene, medium density polyethylene, high density polyethylene, polypropylene, isotactic polypropylene, highly isotactic polypropylene, syndiotactic polypropylene, random copolymer of propylene and ethylene and/or butene and/or hexene, elastomers such as ethylene propylene rubber, ethylene propylene diene monomer rubber, neoprene, and blends of thermoplastic polymers and elastomers, such as for example, thermoplastic elastomers and rubber toughened plastics.

2. Polar Polymers

Preferred polar polymers include homopolymers and copolymers of esters, amides, actates, anhydrides, copolymers of a C2 to C20 olefin, such as ethylene and/or propylene and/or butene with one or more polar monomers such as acetates, anhydrides, esters, alcohol, and or acrylics. Preferred examples include polyesters, polyamides, ethylene vinyl acetate copolymers, and polyvinyl chloride.

3. Cationic polymers Preferred cationic polymers include polymers or copolymers of geminally disubstituted olefins, alpha-heteroatom olefins and/or styrenic monomers. Preferred geminally disubstituted olefins include isobutylene, isopentene, isoheptene, isohexane, isooctene, isodecene, and isododecene. Preferred alpha-heteroatom olefins include vinyl ether and vinyl carbazole, preferred styrenic monomers include styrene, alkyl styrene, para-alkyl styrene, alpha-methyl styrene, chloro-styrene, and bromo-para-methyl styrene. Preferred examples of cationic polymers include butyl rubber, isobutylene copolymerized with para methyl styrene, polystyrene, and poly-alpha-methyl styrene.

4. Miscellaneous

Other preferred layers can be paper, wood, cardboard, metal, metal foils (such as aluminum foil and tin foil), metallized surfaces, glass (including silicon oxide (SiO.x) coatings applied by evaporating silicon oxide onto a film surface), fabric, spunbonded fibers, and non-wovens (particularly polypropylene spun bonded fibers or non-wovens), and substrates coated with inks, dyes, pigments, and the like.

The films may vary in thickness depending on the intended application, however films of a thickness from 1 to 250 μm are usually suitable. Films intended for packaging are usually from 10 to 60 micron thick. The thickness of the sealing layer is typically 0.2 to 50 μm. There may be a sealing layer on both the inner and outer surfaces of the film or the sealing layer may be present on only the inner or the outer surface.

Additives such as block, antiblock, antioxidants, pigments, fillers, processing aids, UV stabilizers, neutralizers, lubricants, surfactants and/or nucleating agents may also be present in one or more than one layer in the films. Preferred additives include silicon dioxide, titanium dioxide, polydimethylsiloxane, talc, dyes, wax, calcium sterate, carbon black, low molecular weight resins and glass beads.

In another embodiment one more layers may be modified by corona treatment, electron beam irradiation, gamma irradiation, or microwave irradiation. In a preferred embodiment one or both of the surface layers is modified by corona treatment.

The films described herein may also comprise from 5 to 60 weight %, based upon the weight of the polymer and the resin, of a hydrocarbon resin. The resin may be combined with the polymer of the seal layer(s) or may be combined with the polymer in the core layer(s). The resin preferably has a softening point above 100° C., even more preferably from 130 to 180° C. Preferred hydrocarbon resins include those described above. The films comprising a hydrocarbon resin may be oriented in uniaxial or biaxial directions to the same or different degrees.

Molded Products

The plasticized polyolefin composition described above may also be used to prepare the radiation resistant molded products of this invention in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art.

The compositions described herein may be shaped into desirable end use articles by any suitable means known in the art. Thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof are typically used methods.

Thermoforming is a process of forming at least one pliable plastic sheet into a desired shape. An embodiment of a thermoforming sequence is described, however this should not be construed as limiting the thermoforming methods useful with the compositions of this invention. First, an extrudate film of the composition of this invention (and any other layers or materials) is placed on a shuttle rack to hold it during heating. The shuttle rack indexes into the oven which pre-heats the film before forming. Once the film is heated, the shuttle rack indexes back to the forming tool. The film is then vacuumed onto the forming tool to hold it in place and the forming tool is closed. The forming tool can be either "male" or "female" type tools. The tool stays closed to cool the film and the tool is then opened. The shaped laminate is then removed from the tool.

Thermoforming is accomplished by vacuum, positive air pressure, plug-assisted vacuum forming, or combinations and variations of these, once the sheet of material reaches thermoforming temperatures, typically of from 140° C. to 185° C. or higher. A pre-stretched bubble step is used, especially on large parts, to improve material distribution. In one embodiment, an articulating rack lifts the heated laminate towards a male forming tool, assisted by the application of a vacuum from orifices in the male forming tool. Once the laminate is firmly formed about the male forming tool, the thermoformed shaped laminate is then cooled, typically by blowers. Plug-assisted forming is generally used for small, deep drawn parts. Plug material, design, and timing can be critical to optimization of the process. Plugs made from insulating foam avoid premature quenching of the plastic. The plug shape is usually similar to the mold cavity, but smaller and without part detail. A round plug bottom will usually promote even material distribution and uniform side-wall thickness. For a semicrystalline polymer such as polypropylene, fast plug speeds generally provide the best material distribution in the part.

The shaped laminate is then cooled in the mold. Sufficient cooling to maintain a mold temperature of 30° C. to 65° C. is desirable. The part is below 90° C. to 100° C. before ejection in one embodiment. For the good behavior in thermoforming, the lowest melt flow rate polymers are desirable. The shaped laminate is then trimmed of excess laminate material.

Blow molding is another suitable forming means, which includes injection blow molding, multi-layer blow molding, extrusion blow molding, and stretch blow molding, and is especially suitable for substantially closed or hollow objects, such as, for example, gas tanks and other fluid containers. Blow molding is described in more detail in, for example, CONCISE ENCYCLOPEDIA OF POLYMER SCIENCE AND ENGINEERING 90-92 (Jacqueline I. Kroschwitz, ed., John Wiley & Sons 1990).

In yet another embodiment of the formation and shaping process, profile co-extrusion can be used. The profile co-extrusion process parameters are as above for the blow molding process, except the die temperatures (dual zone top and bottom) range from 150° C.-235° C., the feed blocks are from 90° C.-250° C., and the water cooling tank temperatures are from 10° C.-40° C.

One embodiment of an injection molding process is described as follows. The shaped laminate is placed into the injection molding tool. The mold is closed and the substrate material is injected into the mold. The substrate material has a melt temperature between 200° C. and 300° C. in one embodiment, and from 215° C. and 250° C. and is injected into the mold at an injection speed of between 2 and 10 seconds. After injection, the material is packed or held at a predetermined time and pressure to make the part dimensionally and aesthetically correct. Typical time periods are from 5 to 25 seconds and pressures from 1,380 kPa to 10,400 kPa. The mold is cooled between 10° C. and 70° C. to cool the substrate. The temperature will depend on the desired gloss and appearance desired. Typical cooling time is from 10 to 30 seconds, depending on part on the thickness. Finally, the mold is opened and the shaped composite article ejected.

Likewise, molded articles may be fabricated by injecting molten polymer into a mold that shapes and solidifies the molten polymer into desirable geometry and thickness of molded articles. Sheet may be made either by extruding a substantially flat profile from a die, onto a chill roll, or alternatively by calendaring. Sheet will generally be considered to have a thickness of from 10 mils to 100 mils (254 μm to 2540 μm), although sheet may be substantially thicker. Tubing or pipe may be obtained by profile extrusion for uses in medical, potable water, land drainage applications or the like. The profile extrusion process involves the extrusion of molten polymer through a die. The extruded tubing or pipe is then solidified by chill water or cooling air into a continuous extruded articles. The tubing will generally be in the range of from 0.31 cm to 2.54 cm in outside diameter, and have a wall thickness of in the range of from 254 μm to 0.5 cm. The pipe will generally be in the range of from 2.54 cm to 254 cm in outside diameter, and have a wall thickness of in the range of from 0.5 cm to 15 cm. Sheet made from the products of an embodiment of a version of the present invention may be used to form containers. Such containers may be formed by thermoforming, solid phase pressure forming, stamping and other shaping techniques. Sheets may also be formed to cover floors or walls or other surfaces.

In an embodiment of the thermoforming process, the oven temperature is between 160° C. and 195° C., the time in the oven between 10 and 20 seconds, and the die temperature, typically a male die, between 10° C. and 71° C. The final thickness of the cooled (room temperature), shaped laminate is from 10 μm to 6000 μm in one embodiment, from 200 μm to 6000 μm in another embodiment, and from 250 μm to 3000 μm in yet another embodiment, and from 500 μm to 1550 μm in yet another embodiment, a desirable range being any combination of any upper thickness limit with any lower thickness limit.

In an embodiment of the injection molding process, wherein a substrate material in injection molded into a tool including the shaped laminate, the melt temperature of the substrate material is between 230° C. and 255° C. in one embodiment, and between 235° C. and 250° C. in another embodiment, the fill time from 2 to 10 seconds in one embodiment, from 2 to 8 seconds in another embodiment, and a tool temperature of from 25° C. to 65° C. in one embodiment, and from 27° C. and 60° C. in another embodiment. In a desirable embodiment, the substrate material is at a temperature that is hot enough to melt any tie-layer material or backing layer to achieve adhesion between the layers.

In yet another embodiment of the invention, the compositions of this invention may be secured to a substrate material using a blow molding operation. Blow molding is particularly useful in such applications as for making closed articles such as fuel tanks and other fluid containers, playground equipment, outdoor furniture and small enclosed structures. In one embodiment of this process, Compositions of this invention are extruded through a multilayer head, followed by placement of the uncooled laminate into a parison in the mold. The mold, with either male or female patterns inside, is then closed and air is blown into the mold to form the part.

It will be understood by those skilled in the art that the steps outlined above may be varied, depending upon the desired result. For example, the an extruded sheet of the compositions of this invention may be directly thermoformed or blow molded without cooling, thus skipping a cooling step. Other parameters may be varied as well in order to achieve a finished composite article having desirable features.

Non-Wovens and Fibers

The plasticized polyolefin composition described above may also be used to prepare radiation resistant nonwoven fabrics and fibers in any nonwoven fabric and fiber making process, including but not limited to, melt blowing, spunbonding, film aperturing, and staple fiber carding, preferably a continuous filament process is used or a spunbonding process is used. Spunbonding generally involves the extrusion of fibers through a spinneret. These fibers are then drawn using high velocity air and laid on an endless belt. A calender roll is generally then used to heat the web and bond the fibers to one another although other techniques may be used such as sonic bonding and adhesive bonding.

Radiation Resistant Applications

The enhanced properties of the plasticized polyolefin compositions described herein are useful in a wide variety of applications where radiation resistance is desired, including articles such as cookware, storageware, toys, medical devices, sterilizable medical devices, sterilization containers, nonwoven fibers and fabrics (including articles therefrom such as drapes, gowns, filters, hygiene products, diapers, and films), oriented films, packaging films, agricultural films, sheets, crates, containers, packaging, wire and cable jacketing, pipes, geomembranes, sporting equipment, tubing, pipes, profiles, instrumentation sample holders and sample windows, outdoor furniture (e.g., garden furniture) and playground equipment. Fabrication of the radiation resistant plasticized polyolefins of the invention to form these articles may be accomplished by injection molding, extrusion, thermoforming, blowing, blow-molding, transfer molding, spunbonding, melt blowing, fiber spinning, stretching for oriented films, compression molding, transfer molding; film blowing, film casting, lamination, pultrusion, protrusion, draw reduction, rotational molding, spinbonding, melt spinning, or combinations thereof and other common processing methods. Use of at least thermoforming or film applications allows for the possibility of and derivation of benefits from uniaxial or biaxial orientation of the radiation tolerant material.

In a preferred embodiment, the plasticized polyolefin compositions of this invention are useful for medical and food packaging, and related applications, as well as for making sterilizable articles themselves. In a preferred embodiment, the radiation resistant and or sterilizable articles prepared from the compositions of this invention include: articles such as storageware, medical devices, sterilizable medical devices, sterilization containers, nonwoven fibers and fabrics (including articles therefrom such as drapes, gowns, filters, hygiene products, diapers, and films), oriented films, packaging films, sheets, containers, packaging, wire and cable jacketing, pipes, tubing, medical tubing, instrumentation sample holders and sample windows, labware, such as roller bottles for culture growth and media bottles.

In a particularly preferred embodiment, the radiation resistant and or sterilizable articles prepared from the compositions of this invention include: articles such as liquid storage containers such as bags, pouches, and bottles for storage and intravenous (IV) infusion of blood or solutions; packaging material including those for any medical device or drugs including unit-dose or other blister or bubble pack as well as for wrapping or containing food preserved by irradiation.

In a particularly preferred embodiment, the radiation resistant and or sterilizable articles prepared from the compositions of this invention include: articles such as medical tubing and valves for any medical device including infusion kits, catheters, and respiratory therapy, as well as packaging materials for medical devices or food which is irradiated including trays, as well as stored liquid, particularly water, milk, or juice, containers including unit servings and bulk storage containers as well as transfer means such as tubing, pipes, and such.

Useful applications of the radiation resistant materials of this invention include food packaging material comprising: film and a self-supporting multilayered structure which includes: 1) metal foil, 2) cellulosic material, 3) opaque plastic film, or combinations thereof. This, of course includes simple wrapping film, film useful for bubble or blister packing, and the materials useful for producing the containers known as "liquid-boxes" as well as other useful pouches, bottles or hybrid-type containers. The useful food packaging materials may be formed by extrusion, blowing, lamination, or combinations thereof.

Preferred medical devices prepared from the radiation resistant materials of this invention include those which are suitable for 1) intravenous (IV) use, 2) transport, storage, dispensing, or combinations thereof of medications, 3) surgical use, 4) medical examination, 5) culture growth, preparation, examination, or combinations thereof, 6) other laboratory operations, or 7) combinations thereof. Such medical devices include such items as 1) IV catheter, probe, expanding device such as an arterial "balloon", or combinations thereof, 2) IV fluid container or dispenser, IV tubing, IV valve, IV injection port, unit-dose package, syringe or syringe barrel, or combinations thereof, 3) forceps, handle or holder for surgical instruments, surgical probe, curette, clamp or tying device, retractor, biopsy sampler, gowns, drapes, masks, filters, filter membranes, caps, booties, or combinations thereof, 4) speculum, probe, retractor, forceps, scraper, sampler, or combinations thereof, 5) culture dish, culture bottle, cuvette, smear slide, smear or sample container, or combinations thereof. Further specific examples of useful medical devices which may be made using the radiation resistant materials of this invention include disposable and reusable hypodermic syringes, particularly the barrels and plunger parts. This would, of course, include prefilled hypodermic syringes for drug packaging and delivery as well as ancillary parts of syringes including needle hubs and needle sheaths. This will also include parts for parenteral kits including valves, cannula hubs, connectors, and cannula shields. Parts for catheters are also included, particularly cannula hubs, connectors, and cannula shields. Useful labware may also be produced including test tubes, culture tubes, and centrifuge tubes as well as vacuum blood collection tubes and ancillary parts including needle adapters/holders, and shields as well as drug vials, caps, and seals. Measuring devices such as droppers, eye-droppers, pipettes, and graduated feeding tubes, cylinders, and burets may also be usefully made by the practice of our invention as well as infant or disabled nursers and nurser holders.

In a preferred embodiment, the above articles are produced from a blend of polypropylene and one or more NFP's. Preferred polymers, including preferred propylene polymers, include those having a heptane insolubles level from about 88 to 99%, preferably from about 90 to 97%.

In another particularly preferred embodiments the propylene polymer used herein is a random copolymer of propylene and ethylene, where the ethylene is present at up to 15 weight % (based upon the weight of the copolymer), preferably at 1 to 10%, more preferably 1.5 to 5 weight %, more preferably 2 to 4 weight % and the polymer has a melt flow rate (MFR) in the range from 0.1 dg/min to 2500 dg/min, preferably from 0.2 to 500 dg/min, preferably from 0.3 to 200 dg/min, preferably from 1 to 100 dg/min, preferably from 5 to 50 dg/min.

In a preferred embodiment, the sterilized article of this invention comprises a polypropylene having a weight average molecular weight of from 10,000 to 400,000 and a molecular weight distribution ($M_w/M_n$) of from 1 to 9, preferably a weight average molecular weight of from 40,000 to 300,000 and a molecular weight distribution of from 1 to 6, preferably a weight average molecular weight of from 50,000 to 200,000 and a molecular weight distribution of from 1 to 4.

The articles manufactured from the blends of this invention exhibit improved resistance to discoloration and embrittlement on exposure to sterilizing doses of high energy radiation, as compared to otherwise identical formulations of polypropylene alone.

In some embodiments, the compositions of this invention are further blended with additives to further enhance the radiation resistance properties. Examples of preferred additives include hindered amine light stabilizer (HALS) such as the 2,2,4,4-tetramethylpiperidine derivatives such as N,N-bis (2,2,6,6-tetramethyl-4-piperidinyl)-1,6-hexanediamine, bis (2,2,6,6-tetramethyl-4-piperidinyl) decanedioate, and the reaction product of dimethyl succinate plus 4-hydroxy-2,2,6, 6-tetramethyl-1-piperidine-ethanol sold by Ciba-Geigy Corporation under the tradenames Chimassorb 944LD, Tinuvin 770, and Tinuvin 622LD, respectively. The HALS is preferably employed at 0.01 to 0.5 wt % of the formulation, preferably from 0.02 to 0.25 wt %, and most preferably from 0.03 to 0.15 wt %.

In some embodiments, the compositions of this invention are further blended with additives to further enhance the radiation resistance properties. Examples of preferred additives include a secondary antioxidant such as those of the thiodipropionate ester and the phosphite types. Preferred examples of the thiodipropionates are distearyl thiodipropionate (DSTDP) and dilaurylthiodipropionate (DLTDP), commercially available from Deer Polymer Corporation. Preferred embodiments of the phosphites are tris(2,4-di-t-butylphenyl)phosphite and bis(2,4-di-t-butylphenyl)pentaerythritol diphosphite available as Irgafos 168 from Ciba-Geigy Corporation and Ultranox 626 available from General Electric Specialty Chemicals, respectively. Additives of this class may be optionally included in the subject blends at up to 1 wt %, preferably at 0.01 to 0.50 wt % by weight of the formulation. Preferably, if used, they would be added at 0.02-0.25 wt % of the formulation, most preferably at 0.03-0.15 wt % of the formulation.

In some embodiments, the compositions of this invention are further blended with additives to further enhance the radiation resistance properties. Examples of preferred additives include additives included for the purpose of providing clarity to the blends of this invention drawn from the general class of compound known as organic nucleating agents. In this class are a wide variety of chemical compositions, including but not limited to salts of benzoic and other organic acids, salts of partially esterified phosphoric acid, and dibenzylidene sorbitols. Preferred are the dibenzylidene sorbitols for their powerful clarifying effects. Most preferred are bis-4-methylbenzylidene sorbitol and bis-3,4,-dimethylbenzylidene sorbitol which are available from Milliken Chemical Company under the tradenames Millad 3940 and Millad 3988 respectively. When included in the formulations of the subject materials, these clarifying nucleators are used at from 0.05 to 1.0 wt % by weight of the composition, preferably from 0.1 to 0.5 wt %, and most preferably from 0.15 to 0.35 wt %.

In all of the above cases, the additives described may be incorporated into the blends of this invention as part of either of the major polymeric components of the blend or as an additional component added to the blend itself.

In a preferred embodiment, the polyolefin is polypropylene, the NFP is a PAO and the blend is formed into an article and thereafter subjected to radiation. Preferred articles comprising the blends of this invention that have been subjected to sterilizing amounts of radiation include films, sheets, fibers, woven and nonwoven fabrics, tubes, pipes, automotive components, furniture, sporting equipment, food storage containers, transparent and semi-transparent articles, toys, tubing and pipes, and medical devices.

The plasticized polyolefin compositions of this invention, either as the polymeric material per se, or as an article, e.g., a syringe or package film, can be sterilized by subjecting the polymer to a sterilizing amount of high energy radiation. The high energy radiation can be provided by any one of a variety of sources, including beta radiation, such as from an electron beam, or gamma radiation, such as from a cobalt-60 source, high energy electrons and X-rays. In general, the sterilizing radiation doses are on the order of from 0.5 to 5.0 megarads (MRad), with the typical dose being 1.0 to 3.5 megarads. It is to be understood that higher doses, such as up to 10 megarads, could be employed, but are generally not necessary.

In a preferred embodiment, the sterilized articles show increased radiation tolerance as evidenced by at least 20% greater Gardner impact strength after treatment with up to 10 MRads of gamma or beta radiation than would be found for the same article made from the polypropylene alone which has been subjected to the same radiation dose, preferably by at least 50% greater, more preferably by at least 100% greater, more preferably by at least 200% greater, more preferably by at least 300% greater.

In a preferred embodiment, the sterilized articles produced exhibit increased radiation tolerance as evidenced by at least 20% greater Gardner impact strength per percent of non-functionalized plasticizer present after treatment with up to 10 MRads of gamma or beta radiation than would be found for the same article made from the polypropylene alone which has been subjected to the same radiation dose, preferably by at least 50% greater per percent of non-functionalized plasticizer present, more preferably by at least 100% greater per percent of non-functionalized plasticizer present, more preferably by at least 200% greater per percent of non-functionalized plasticizer present, more preferably by at least 300% greater per percent of non-functionalized plasticizer present.

Test Methods

Fluid Properties

Kinematic Viscosity (KV) is measured by ASTM D445. Viscosity index (VI) is determined by ASTM D2270. Pour Point is measured by ASTM D97. The number-average molecular weight ($M_n$) can be determined by Gas Chromatography (GC), as described in "Modern Practice of Gas Chromatography", R. L. Grob and E. F. Barry, Wiley-Interscience, 3rd Edition (July 1995); or determined by Gel Permeation Chromatography (GPC), as described in "Modern Size Exclusion Liquid Chromatographs", W. W. Yan, J. J. Kirkland, and D. D. Bly, J. Wiley & Sons (1979); or estimated by ASTM D 2502; or estimated by freezing point depression, as described in "Lange's Handbook of Chemistry", 15th Edition, McGrawHill. The average carbon number ($C_n$) is calculated from $M_n$ by $C_n=M_n/14$.

Melt Flow Rate

The Melt Flow Rate (MFR) is measured according to ASTM D1238 at 230° C., under a load of 2.16 kg unless otherwise noted. The units for MFR are "g/10 min" or the equivalent "dg/min."

Mechanical Properties

Tensile properties at room temperature (23±2° C.) were determined according to ASTM D638, including Young's modulus (also called modulus of elasticity), yield stress (also called tensile strength at yield), yield strain (also called elongation at yield), break stress (also called tensile strength at break), and break strain (also called elongation at break). Injection-molded tensile bars were of ASTM D638 Type I or Type IV geometry, tested at a speed of 2 inch/min.

Flexure properties at room temperature were determined according to ASTM D790A, including the 1% secant modulus, using a 2 inch support span.

Notched Izod impact strength was determined according to ASTM D256, at room temperature. A TMI Izod Impact Tester was used. Specimens were made by either cutting injection-molded ASTM D790 "Molding Materials (Thermoplastics and Thermosets)" bars in half or cutting the middle out of an injection-molded ASTM D638 Type I tensile bar.

Gardner impact strength at room temperature was measured according to ASTM D5420 on injection molded disks (3.5 inch diameter×0.125 inch thick).

Heat deflection temperature (HDT) was measured according to ASTM D648 on injection molded flexure bars, at 66 psi load.

Color

Color was measured on compression molded disks using a Hunter Color Quest XE colorimeter CQX2391 (Hunter Associates Laboratories, Inc.). The test was run according to the protocol developed by the instrument manufacturer, with reference to ASTM E1164. Measurements were made using the D/65 illuminant (light source), 10° observer, and the port in the closed position. Other color scales and measurement instruments could be substituted in work of this type with comparable relative results. On the Hunter "B" scale employed here, 0.0 is considered pure white. Negative values are more blue; positive values are more yellow. The departure from pure white increases with the absolute value of the Hunter "B" scale. Generally, white polymers are more desirable than yellowish ones.

Emissions Testing

The permanence of a fluid in a resin was assessed using a TGA retention test. A Perkin-Elmer TGA 7 was used to measure the weight loss from a sample in a nitrogen atmosphere. Specimens of 10 mil in thickness and 5 mg in weight were prepared by compression molding, then placed in the sample holder (located in the test chamber, which was purged with nitrogen throughout the test). The temperature in the test chamber was then ramped from ambient to 200° C. at 200° C./min, and held at 200° C. for 120 minutes. The weight change as a function of time was recorded. The percentage of fluid remaining in the resin after 120 minutes was determined by % TGA retention=(total weight % loss)/(initial weight fraction of fluid).

Dynamic Mechanical Thermal Analysis

The glass transition temperature ($T_g$) was measured using dynamic mechanical thermal analysis (DMTA). This test provides information about the small-strain mechanical response (relaxation behavior) of a sample as a function of temperature over a temperature range that includes the glass transition region and the visco-elastic region prior to melting.

Typically, samples were tested using a three point bending configuration (TA Instruments DMA 2980). A solid rectangular compression molded bar was placed on two fixed supports; a movable clamp applied a periodic deformation to the sample midpoint at a frequency of 1 Hz and an amplitude of 20 μm. The sample was initially cooled to −130° C. then heated to 60° C. at a heating rate of 3° C./min. In some cases, compression molded bars were tested using other deformation configurations, namely dual cantilever bending and tensile elongation (Rheometrics RSAII). The periodic deformation under these configurations was applied at a frequency of 1 Hz and strain amplitude of 0.05%. The sample was cooled to −130° C. and then heated to 60° C. at a rate of 2° C./min. The slightly difference in heating rate does not influence the glass transition temperature measurements significantly.

The output of these DMTA experiments is the storage modulus (E') and loss modulus (E"). The storage modulus measures the elastic response or the ability of the material to store energy, and the loss modulus measures the viscous response or the ability of the material to dissipate energy. Tan δ is the ratio of E"/E' and gives a measure of the damping ability of the material. The beginning of the broad glass transition (β-relaxation) is identified as the extrapolated tangent to the Tan δ peak. In addition, the peak temperature and area under the peak are also measured to more fully characterize the transition from glassy to visco-elastic region.

Differential Scanning Calorimetry

Crystallization temperature ($T_c$) and melting temperature ($T_m$) were measured using Differential Scanning Calorimetry (DSC). This analysis was conducted using either a TA Instruments MDSC 2920 or a Perkin Elmer DSC7. Typically, 6 to 10 mg of molded polymer or plasticized polymer was sealed in an aluminum pan and loaded into the instrument at room temperature. Melting data (first heat) were acquired by heating the sample to at least 30° C. above its melting temperature at a heating rate of 10° C./min. This provides information on the melting behavior under as-molded conditions, which can be influenced by thermal history as well as any molded-in orientation or stresses. The sample was then held for 10 minutes at this temperature to destroy its thermal history. Crystallization data was acquired by cooling the sample from the melt to at least 50° C. below the crystallization temperature at a cooling rate of 10° C./min. The sample was then held at 25° C. for 10 minutes, and finally heated at 10° C./min to acquire additional melting data (second heat). This provides information about the melting behavior after a controlled thermal history and free from potential molded-in orientation and stress effects. The endothermic melting transition (first and second heat) and exothermic crystallization transition were analyzed for onset of transition and peak temperature. The melting temperatures reported in the tables are the peak melting temperatures from the second heat unless otherwise indicated. For polymers displaying multiple peaks, the higher melting peak temperature is reported.

Areas under the curve was used to determine the heat of fusion ($\Delta H_f$) which can be used to calculate the degree of crystallinity. A value of 207 J/g was used as the equilibrium heat of fusion for 100% crystalline polypropylene (obtained from B. Wunderlich, "Thermal Analysis", Academic Press, Page 418, 1990). The percent crystallinity is calculated using the formula, [area under the curve (J/g)/207 (J/g)]*100.

Size-Exclusion Chromatography of Polymers

Molecular weight distribution was characterized using Size-Exclusion Chromatography (SEC). Molecular weight (weight-average molecular weight, $M_w$, and number-average molecular weight, $M_n$) were determined using a High Temperature Size Exclusion Chromatograph (either from Waters Corporation or Polymer Laboratories), equipped with a differential refractive index detector (DRI), an online light scattering detector, and a viscometer. Experimental details not described below, including how the detectors were calibrated, are described in: T. Sun, P. Brant, R. R. Chance, and W. W. Graessley, Macromolecules, Volume 34, Number 19, 6812-6820, (2001).

Three Polymer Laboratories PLgel 10 mm Mixed-B columns were used. The nominal flow rate was 0.5 cm³/min, and the nominal injection volume was 300 µL. The various transfer lines, columns and differential refractometer (the DRI detector) were contained in an oven maintained at 135° C.

Solvent for the SEC experiment was prepared by dissolving 6 grams of butylated hydroxy toluene as an antioxidant in 4 liters of Aldrich reagent grade 1,2,4 trichlorobenzene (TCB). The TCB mixture was then filtered through a 0.7 µm glass pre-filter and subsequently through a 0.1 µm Teflon filter. The TCB was then degassed with an online degasser before entering the SEC.

Polymer solutions were prepared by placing dry polymer in a glass container, adding the desired amount of TCB, then heating the mixture at 160° C. with continuous agitation for about 2 hours. All quantities were measured gravimetrically. The TCB densities used to express the polymer concentration in mass/volume units are 1.463 g/ml at room temperature and 1.324 g/ml at 135° C. The injection concentration ranged from 1.0 to 2.0 mg/ml, with lower concentrations being used for higher molecular weight samples.

Prior to running each sample the DRI detector and the injector were purged. Flow rate in the apparatus was then increased to 0.5 ml/minute, and the DRI was allowed to stabilize for 8-9 hours before injecting the first sample. The LS laser was turned on 1 to 1.5 hours before running samples.

The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the same as described below for the LS analysis. Units on parameters throughout this description of the SEC method are such that concentration is expressed in g/cm³, molecular weight is expressed in g/mole, and intrinsic viscosity is expressed in dL/g.

The light scattering detector used was a Wyatt Technology High Temperature mini-DAWN. The polymer molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{MP(\theta)} + 2A_c c$$

Here, $\Delta R(\theta)$ is the measured excess Rayleigh scattering intensity at scattering angle $\theta$, c is the polymer concentration determined from the DRI analysis, $A_2$ is the second virial coefficient, $P(\theta)$ is the form factor for a monodisperse random coil (described in the above reference), and $K_o$ is the optical constant for the system:

$$K_o = \frac{4\pi^2 n^2 \left(\frac{dn}{dc}\right)^2}{\lambda^4 N_A}$$

in which $N_A$ is Avogadro's number, and (dn/dc) is the refractive index increment for the system. The refractive index, n=1.500 for TCB at 135° C. and λ=690 nm. In addition, $A_2$=0.0006 for propylene polymers and 0.0015 for butene polymers, and (dn/dc)=0.104 for propylene polymers and 0.098 for butene polymers.

A high temperature Viscotek Corporation viscometer was used, which has four capillaries arranged in a Wheatstone bridge configuration with two pressure transducers. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [η], at each point in the chromatogram is calculated from the following equation:

$$\eta_s = c[\eta] + 0.3(c[\eta])^2$$

where c was determined from the DRI output.

The branching index (g') is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromotographic slices, i, between the integration limits. The branching index g' is defined as:

$$g' = \frac{[\eta]_{avg}}{k M_v^\alpha}$$

where k=0.0002288 and α=0.705 for propylene polymers, and k=0.00018 and α=0.7 for butene polymers. $M_v$ is the viscosity-average molecular weight based on molecular weights determined by LS analysis.

¹³C-NMR Spectroscopy

Polymer microstructure was determined by ¹³C-NMR spectroscopy, including the concentration of isotactic and syndiotactic diads ([m] and [r]), triads ([mm] and [rr]), and pentads ([mmmm] and [rrrr]). Samples were dissolved in $d_2$-1,1,2,2-tetrachloroethane. Spectra were recorded at 125°

C. using a NMR spectrometer of 75 or 100 MHz. Polymer resonance peaks are referenced to mmmm=21.8 ppm. Calculations involved in the characterization of polymers by NMR follow the work of F. A. Bovey in "Polymer Conformation and Configuration" Academic Press, New York 1969 and J. Randall in "Polymer Sequence Determination, $^{13}$C-NMR Method", Academic Press, New York, 1977. The percent of methylene sequences of two in length, % $(CH_2)_2$, were calculated as follows: the integral of the methyl carbons between 14-18 ppm (which are equivalent in concentration to the number of methylenes in sequences of two in length) divided by the sum of the integral of the methylene sequences of one in length between 45-49 ppm and the integral of the methyl carbons between 14-18 ppm, times 100. This is a minimum calculation for the amount of methylene groups contained in a sequence of two or more since methylene sequences of greater than two have been excluded. Assignments were based on H. N. Cheng and J. A. Ewen, Makromol. Chem. 1989, 190, 1931.

Processing Methods

Blending

The components of the present invention can be blended by any suitable means. For example, they may be blended in a static mixer, batch mixer, extruder, or a combination thereof, that is sufficient to achieve an adequate dispersion of plasticizer in the polymer. The mixing step may involve first dry blending using, for example, a tumble blender. It may also involve a "master batch" approach, where the final plasticizer concentration is achieved by combining neat polymer with an appropriate amount of plasticized polymer that had been previously prepared at a higher plasticizer concentration. Dispersion may take place as part of a processing method used to fabricate articles, such as in the extruder on an injection molding machine or blown-film line.

Two general methods were used to generate examples of plasticized blends. The first method, which is referred to as the Extruder Method, involved "dry blending" polymer granules or pellets with appropriate amounts of plasticizer and an additive package (including, for example, antioxidants) in a tumble blender to achieve a homogeneous mixing of components at the desired plasticizer and additive concentrations. This was followed by compounding and pelletizing the blend using an extruder (single-screw or twin-screw) at an appropriate extrusion temperature above the melting point of the polymer.

The second method, which is referred to as the Brabender Method, involved mixing polymer pellets with the plasticizer in a heated C. W. Brabender Instruments Plasticorder to achieve a homogeneous melt at the desired plasticizer concentration. The Brabender was equipped with a Prep-Mixer head (approximately 200 cm$^3$ volume) and roller blades. The operating temperature was above the melting point of the polymer, typically in the range of 180 to 200° C. Polymer was first melted in the Brabender at 60 RPM. Then, while mixing, fluid was added slowly to prevent pooling in the melted polymer. The blend was then mixed for 5 minutes at 60 RPM under a nitrogen purge. The Brabender was opened and the melt removed from the mixing head and blades as quickly as possible, and allowed to solidify. For those blends later subjected to injection molding, the pieces of material from the Brabender were cut into smaller pieces using a guillotine, then ground into even smaller pieces using a Wiley Mill.

Injection Molding

ASTM-family tensile bars, flexure bars, and impact disks were molded using Van Dorn (70 ton) or Nissei (20 ton) injection molding equipment following ASTM D4101. When the Nissei equipment was used, the following deviations from ASTM D401 were made: ASTM D638 Type IV tensile bars and ASTM D790 flexure bars were molded using a mold temperature of 40° C. and inject time of 30 seconds.

Compression Molding

The following is a description of a typical compression molding protocol. Material to be molded was placed between two sheets of Mylar in a heated press, with the platens kept between 190° C. and 200° C. for at least 5 minutes. The pressure and weight of sample used was adjusted so that the thickness of the film samples was kept close to 4 mil.

Radiation and Aging

Molded specimens were subjected to gamma-radiation treatment from a $^{60}$Co (cobalt-60 isotope) source at approximately 1 MRad/hr rate by STERIS Isomedix Services (Morton Grove, Ill.). Accelerated aging is done by placing the sample in an oven at 60° C. for 2-3 days.

Methods for Determining NFP Content in Blend

Method 1: Extraction

One method to determine the amount of NFP in a blend is Soxhlet extraction, wherein at least a majority of the NFP is extracted with refluxing n-heptane. Analysis of the base polymer is also required because it may contain low molecular weight and/or amorphous material that is soluble in refluxing n-heptane. The level of plasticizer in the blend is determined by correcting its extractables level, in weight percent, by the extractables level for the base polymer, as described below.

The Soxhlet extraction apparatus consists of a 400 ml Soxhlet extractor, with a widened overflow tube (to prevent siphoning and to provide constant flow extraction); a metal screen cage fitted inside the main Soxhlet chamber; a Soxhlet extraction thimble (Whatman, single thickness, cellulose) placed inside the screen cage; a condenser with cooling water and drain; and a one-neck 1000 ml round bottom flask with appropriately sized stir bar and heating mantle.

The procedure is as follows. Dry the soxhlet thimbles in a 95° C. oven for ~60 minutes. Weigh the dry thimble directly after removal from oven; record this weight as A: Thimble Weight Before, in g. Weigh out 15-20 grams of sample (either in pellet or ground pellet form) into the thimble; record as B: Polymer Weight, in g. Place the thimble containing the polymer in the Soxhlet apparatus. Pour about 300 ml of HPLC-grade n-heptane into the round bottom flask with stir bar and secure the flask on the heating mantle. Connect the round bottom flask, the soxhlet, and the condenser in series. Pour more n-heptane down through the center of the condenser into the Soxhlet main chamber until the solvent level is just below the top of the overflow tube. Turn on the cooling water to the condenser. Turn on the heating mantle and adjust the setting to generate a rolling boil in the round bottom flask and maintain a good reflux. Allow to reflux for 16 hours. Turn the heat off but leave the cooling system on. Allow the system to cool down to room temperature. Disassemble the apparatus. Remove the thimble and rinse with a small amount of fresh n-heptane. Allow to air dry in the laboratory hood, followed by oven drying at 95° C. for 90 minutes. Weigh the thimble containing the polymer directly after removal from oven; record as C: Polymer/Thimble Weight After, in g.

The quantity of extract is determined by calculating the weight loss from the sample, W=(A+B−C), in g. The extractables level, E, in weight percent, is then calculated by E=100 (W/B). The plasticizer content in the blend, P, in weight percent, is calculated by P=E(blend)−E(base polymer).

Method 2: Crystallization Analysis Fractionation (CRYSTAF)

Another method to determine the amount of NFP in a blend is fractionation using the Crystallization Analysis Fractionation (CRYSTAF) technique. This technique involves dissolving a sample in a solvent at high temperature, then cooling the solution slowly to cause fractionation of the sample based on solubility. For semi-crystalline samples, including blends, solubility depends primarily on crystallizability: portions of the sample that are more crystalline will precipitate out of solution at a higher temperature than portions of the sample that are less crystalline. The relative amount of sample in solution as a function of temperature is measured using an infrared (IR) detector to obtain the cumulative solubility distribution. The soluble fraction (SF) is defined as the IR signal at the lowest temperature divided by the IR signal when all the sample is dissolved at high temperature, and corresponds to the weight fraction of sample that has not crystallized.

In the case of plasticized polyolefins, the plasticizer is mostly amorphous and therefore contributes to the SF. Thus, the SF will be larger for blends with higher plasticizer content. This relationship is exploited to determine the plasticizer content of a blend of known composition (polymer and plasticizer types) but unknown concentration. A calibration curve that describes the SF as a function of plasticizer content is developed by making a series of physical blends of known concentration using the same polymer and plasticizer materials, and then analyzing these blends under the same run conditions as used for blends of unknown concentration. This series of calibrants must include plasticizer concentrations above and below the concentration of the unknown sample(s), but not greater than 50 weight percent plasticizer, in order to reliably apply the calibration curve to the unknown sample(s). Typically, a linear fit of the calibration points is found to provide a good description of the SF as a function of plasticizer content ($R^2 > 0.9$); other functional forms with 2 or fewer fitting parameters may be used if they improve the goodness-of-fit (increase $R^2$).

A commercial CRYSTAF 200 instrument (Polymer Char S. A., Valencia, Spain) with five stirred stainless steel vessels of 60 mL volume was used to perform this test. Approximately 30 mg of sample were dissolved for 60 min at 160° C. in 30 mL of 1,2-dichlorobenzene that was stabilized with 2 g/4 L of butylated hydroxytoluene. The solution was then stabilized for 45 min at 100° C. The crystallization was carried out from 100 to 30° C. at a crystallization rate of 0.2° C./min. A dual wavelength infrared detector with a heated flow through cell maintained at 150° C. was used to measure the polymer concentration in solution at regular intervals during the crystallization cycle; the measuring wavelength was 3.5 μm and the reference wavelength was 3.6 μm.

EXAMPLES

The present invention, while not meant to be limiting by, may be better understood by reference to the following examples and tables. The polypropylene resins and fluids used in these examples are described in Tables 1 and 2.

TABLE 1

List of Polymers in Examples

| Polymer | Description | Commercial Source |
|---|---|---|
| mPP | isotactic polypropylene homopolymer, synthesized using an Exxpol ® metallocene catalyst; MFR ~16 dg/min | Achieve ™ 1654, ExxonMobil Chemical |
| znPP | experimental isotactic polypropylene homopolymer, synthesized using a Ziegler-Natta catalyst; MFR ~20 dg/min; $M_w/M_n > 3.5$; additive package consisting of 1000 ppm Tinuvin 770 (Ciba Geigy), 300 ppm calcium stearate | — |
| mRCP | experimental propylene-ethylene random copolymer, synthesized using an Exxpol ® metallocene catalyst that makes isotactic polypropylene in the absence of ethylene comonomer; MFR ~24 dg/min; peak melting temperature ~131° C.; $M_w/M_n < 2.3$; ethylene content ~3 wt %; additive package consisting of 800 ppm calcium stearate, 800 ppm Ultranox 626A (General Electric), 500 ppm Tinuvin 622 (Ciba Geigy), and 2500 ppm Millad 3940 (Milliken) | — |
| znRCP | clarified propylene-ethylene random copolymer, synthesized using a Ziegler-Natta catalyst that makes isotactic polypropylene in the absence of ethylene comonomer; MFR ~12 dg/min | PD9374MED ExxonMobil Chemical |

TABLE 2a

List of Fluids and Polymer Modifiers in Examples

| Modifier | Description | Commercial Source |
|---|---|---|
| PAO-6 | poly(alpha-olefin) fluid | SHF-61 or SpectraSyn ™ 6, ExxonMobil Chemical |
| PAO-10 | poly(alpha-olefin) fluid | SHF-101 or SpectraSyn ™ 10, ExxonMobil Chemical |
| PAO-40 | poly(alpha-olefin) fluid | SHF-403 or SpectraSyn ™ 40, ExxonMobil Chemical |
| Isopar | isoparaffinic hydrocarbon fluid | IsoPar ™ V, ExxonMobil Chemical |
| PB | poly(n-butene) fluid | C9900, Infineum |
| mineral oil | white mineral oil fluid | Drakeol ® 34, Penreco |
| PIB-A | polyisobutylene fluid | TPC-137, Texas Petrochemicals |
| PIB-B | polyisobutylene fluid | TPC-1350, Texas Petrochemicals |
| plastomer | ethylene-butene copolymer; melt index ~35 dg/min (ASTM D1238, 190° C., 2.16 kg load); density ~0.882 g/cm$^3$ | Exact ® 4023, ExxonMobil Chemical |

TABLE 2b

Properties of Fluids in Examples

| Fluid | KV @ 100° C. | VI | Pour Point | $M_n$ ($C_n$) |
|---|---|---|---|---|
| PAO-6 | 6 cSt | 138 | −57° C. | 540 g/mole (38) |
| PAO-10 | 10 cSt | 137 | −54° C. | 720 g/mole (51) |
| PAO-40 | 40 cSt | 147 | −39° C. | 1,700 g/mole (121) |
| Isopar | | | −63° C. | 240 g/mole (17) |
| PB | 12 cSt | 60 | −36° C. | 540 g/mole (39) |
| mineral oil | 9 cSt | | −9° C. | 490 g/mole (35) |
| PIB-A | 6 cSt | 132 | −51° C. | 350 g/mole (25) |
| PIB-B | 4000 cSt | | | 3,500 g/mole (250) |

Examples in Tables 3 and 4

Blends of random copolymer polypropylene (RCP) and 10% of fluid were prepared by melt-mixing in a single-screw compounding extruder (Extruder Method). Standard ASTM test specimens were prepared using a 70-ton injection molder. Some of the molded specimens were subjected to 7.5 MRad of gamma-radiation and then aged in an oven at 60° C. for three weeks prior to testing. Others were subjected only to the aging protocol prior to testing.

As expected, exposure to radiation causes the polypropylene to become embrittled; this is most dramatically seen in the Gardner impact data. Addition of fluid allows the impact strength to be substantially retained, or even improved, after radiation dosing and aging. Color after radiation dosing is also improved by fluid modification if the RCP was synthesized using a metallocene catalyst (mRCP), for which the neat resin suffers significant yellowing when irradiated. Color is not changed much by radiation if the RCP was synthesized using a Ziegler-Natta catalyst (znRCP), but the resin is more embrittled (as evidenced in the drop in tensile strength and elongation at yield) than is mRCP, and this effect is offset by the addition of fluid. Thus, modification of both types of RCP with fluid provides an improved balance of color and toughness after radiation treatment compared to the unmodified resin.

TABLE 3

Effect of 7.5 MRad dose of radiation and oven aging at 60° C. for three weeks on properties of mRCP.

| | | Radiated & Aged | | |
|---|---|---|---|---|
| | Neat resin (untreated) | No fluid | 10% Isopar | 10% PAO-10 |
| Mechanical Properties | | | | |
| Tensile Strength @ Yield (kpsi) | 4.0 | 4.7 | 3.5 | 3.6 |
| Elongation @ Yield (%) | 12 | 13 | 20 | 20 |
| Young's Modulus (MPa) | 1698 | 1408 | 460 | 568 |
| Flexural Modulus, 1% Secant (kpsi) | 144 | 145 | 78 | 91 |

TABLE 3-continued

Effect of 7.5 MRad dose of radiation and oven aging at 60° C. for three weeks on properties of mRCP.

| | | Radiated & Aged | | |
|---|---|---|---|---|
| | Neat resin (untreated) | No fluid | 10% Isopar | 10% PAO-10 |
| Gardner Impact, 23° C. (in-lbs) | 230 | 9 | 190 | 197 |
| Notched Izod, 23° C. (ft-lbs/in) | 1.0 | 1.0 | 1.9 | 1.5 |
| Color | | | | |
| Hunter "B" | 1.8 | 13.3 | 6.9 | 6.9 |

TABLE 4

Effect of 7.5 MRad dose of radiation and oven aging at 60° C. for three weeks on properties of znRCP.

| | | Radiated & Aged | | |
|---|---|---|---|---|
| | Neat resin (untreated) | No fluid | 10% Isopar | 10% PAO-10 |
| Mechanical Properties | | | | |
| Tensile Strength @ Yield (kpsi) | 4.4 | 2.8 | 4.2 | 4.1 |
| Elongation @ Yield (%) | 12 | 2 | 18 | 17 |
| Flexural Modulus, 1% Secant (kpsi) | 164 | 165 | 107 | 114 |
| Gardner Impact, 23° C. (in-lbs) | 197 | 2 | 134 | 171 |
| Notched Izod, 23° C. (ft-lbs/in) | 1.1 | 0.9 | 1.2 | 1.2 |
| Color | | | | |
| Hunter "B" | 1.1 | 3.3 | 5.4 | 5.1 |

Examples in Table 5

Blends of Ziegler-Natta homopolymer polypropylene and 5% of fluid were prepared by melt-mixing in a single-screw compounding extruder (Extruder Method). Standard ASTM test specimens were prepared using a 70-ton injection molder. Some of the molded specimens were subjected to 7.5 MRad of gamma-radiation and then aged in an oven at 60° C. for two weeks prior to testing. Others were subjected only to the aging protocol prior to testing.

Modification of the polypropylene resin by addition of fluid results in a softer material, as evidenced by a lower flexure modulus, but only a slight (<1° C. per wt % fluid) decrease in heat deflection temperature (HDT). Radiation does not substantially affect these properties, since they depend on the overall degree of crystallinity and melting point of those crystals. However, radiation does cause a dramatic deterioration of impact properties, and fluid modification provides a means to retain impact strength after radiation treatment at a level much higher than for the neat resin. Color is not affected by addition of these fluids in this resin.

TABLE 5

Effect of increasing doses of radiation and oven aging at 60° C. for three weeks on properties of znPP.

| | Radiation Treatment Level | znPP + fluid added | | | | |
|---|---|---|---|---|---|---|
| Mechanical Property | (MRad) | neat polymer | 5 wt % mineral oil | 5 wt % PAO-6 | 5 wt % PAO-10 | 5 wt % PAO-40 |
| Tensile Elongation at Break (%) | 0 | 19 | 29 | 36 | 35 | 32 |
| | 3 | 19 | 33 | 27 | 28 | 31 |
| | 6 | 9 | 24 | 21 | 24 | 27 |

TABLE 5-continued

Effect of increasing doses of radiation and oven aging at 60° C. for three weeks on properties of znPP.

| Mechanical Property | Radiation Treatment Level (MRad) ↓ | znPP + fluid added | | | | |
|---|---|---|---|---|---|---|
| | | neat polymer | 5 wt % mineral oil | 5 wt % PAO-6 | 5 wt % PAO-10 | 5 wt % PAO-40 |
| Flexure Modulus, | 0 | 222 | 157 | 156 | 158 | 171 |
| 1% secant (psi) | 3 | 231 | 162 | 156 | 161 | 176 |
| | 6 | 235 | 163 | 160 | 165 | 178 |
| HDT | 0 | 106 | 102 | 103 | 102 | 102 |
| (° C.) | 3 | 107 | 102 | 104 | 103 | 102 |
| | 6 | 108 | 104 | 105 | 105 | 104 |
| Gardner impact, | 0 | 38 | 121 | 47 | 113 | 84 |
| 23° C. (lbs-in) | 3 | 6 | 51 | 30 | 61 | 25 |
| | 6 | 1 | 18 | 10 | 18 | 6 |
| Color, Hunter "B" | 0 | 3.0 | 2.8 | 3.0 | 2.8 | 2.8 |
| | 3 | 3.6 | 3.4 | 3.6 | 3.5 | 3.5 |
| | 6 | 3.9 | 3.7 | 3.9 | 3.7 | 3.6 |

Examples in Tables 6 and 7

Blends of polypropylene resin with 10 wt % of different modifiers were prepared by melt-mixing using the Brabender method. ASTM tensile and flexure test specimens were injection molded on a 20-ton injection molder; notched Izod specimens were created by cutting flexure bars in half. Color disks were prepared by compression molding at 220° C. under 25 tons pressure. Some of the molded specimens were dosed with 6 MRad of gamma radiation and tested without oven aging. Others were tested without radiation treatment and without oven aging.

Again, it is found that addition of fluid both softens and toughens polypropylene. Furthermore, it is also found again that radiation treatment does not influence the stiffness of the resin, whether unmodified or modified by addition of fluid. However, the presence of fluid does allow improved impact strength after radiation treatment relative to the irradiated neat resin. Also, the presence of fluid substantially improves the color characteristics after radiation treatment relative to the irradiated neat resin. In contrast, use of the same amount of a plastomer modifier does not achieve consistent improvements in toughness after irradiation (it does much poorer job in mPP for instance), and does not protect against yellowing. The TGA retention data shows that PB and PIB are not preferred fluids since they have high emission rates, and that PAO is preferred over mineral oil since the emission rate for PAO is lower than for mineral oil despite essentially equivalent viscosities (as measured by KV at 100° C.) and it offers better protection against yellowing due to irradiation.

TABLE 6

Effect of 6 MRad of gamma-radiation on properties of mPP.

| Property | Dose (MRad) | neat polymer | 10 wt % mineral oil | 10 wt % PAO-10 | 10 wt % PB | 10 wt % PIB-A | 10 wt % plastomer |
|---|---|---|---|---|---|---|---|
| Young's | 0 | 126 | 72 | 67 | 73 | 72 | 106 |
| modulus (kpsi) | 6 | 133 | 73 | 73 | 74 | 73 | 107 |
| Notched Izod, | 0 | 9.4 | 31.7 | 30.8 | 31.0 | 29.6 | 19.2 |
| 23° C. (ft-lb/in) | 6 | 6.0 | 27.4 | 26.9 | 22.9 | 26.9 | 10.9 |
| Color, | 0 | 4.8 | 4.5 | 3.2 | 6.6 | 6.1 | 4.4 |
| Hunter "B" | 6 | 18.7 | 8.9 | 6.6 | 7.5 | 5.9 | 21.4 |
| TGA retention (%) | 0 | 0 | 8 | 4 | 32 | 62 | 0 |

TABLE 7

Effect of 6 MRad of gamma-radiation on properties of znRCP.

| Property | Dose (MRad) | neat polymer | 10 wt % mineral oil | 10 wt % PAO-10 | 10 wt % AN | 10 wt % plastomer |
|---|---|---|---|---|---|---|
| Young's | 0 | 90 | 54 | 48 | 55 | 78 |
| modulus (kpsi) | 6 | 94 | 55 | 54 | 54 | 74 |
| Notched Izod, | 0 | 1.1 | 1.8 | 3.6 | 2.4 | 4.0 |
| 23° C. (ft-lb/in) | 6 | 0.9 | 1.2 | 1.5 | 1.4 | 1.7 |
| Color, | 0 | 4.8 | 3.8 | 4.4 | 7.7 | 3.1 |
| Hunter "B" | 6 | 9.7 | 6.2 | 6.0 | 8.6 | 9.9 |

Examples in Table 8

The improvement in radiation resistance of polypropylene due to addition of liquid polyisobutylene was measured. Blends of mPP with 5 and 10 wt % of two different PIB liquids were made by melt mixing using the Brabender method. Samples of neat mPP and the four blends were compression-molded into film specimens, and subjected to gamma-radiation treatment at three dose levels (2.5, 5, and 10 MRad). The effect of radiation on the PP resin was assessed by small-amplitude oscillatory shear rheology at 190° C., using a Rheometrics Scientific ARES rheometer. For each sample, the dynamic shear viscosity was measured as a function of frequency, over a range of 100 to 0.1 radian/s (rad/s), at a temperature of 190° C. A decrease in viscosity after radiation treatment indicates degradation of molecular weight, which has a detrimental effect on mechanical properties of the resin.

The effect of radiation treatment on the dynamic viscosity for neat and modified mPP is described in Table 8 in terms of the "relative viscosity" at the highest and lowest frequencies examined. The relative viscosity is defined as the dynamic viscosity after radiation treatment at the specified frequency, divided by the dynamic viscosity before radiation treatment at the same frequency. The dynamic viscosity at 0.1 rad/s corresponds to a low-shear viscosity, which should closely approximate the so-called zero-shear viscosity, no, that is known to depend strongly on molecular weight. The dynamic viscosity at 100 rad/s corresponds to a high-shear viscosity that is more relevant to polymer processing, which depends on the molecular weight and shear-thinning characteristics of the material.

Radiation treatment results in a substantial decrease in viscosity of all the samples at all frequencies. However, the addition of PIB clearly improves the radiation resistance of the PP resin, as evidence by a greater relative viscosity for the blends than for the neat PP. In all instances, the addition of PIB reduces the loss in viscosity suffered upon radiation treatment, which corresponds to less degradation in PP molecular weight.

TABLE 8

Effect of gamma-radiation on rheology of neat mPP and mPP + PIB blends.

| Sample | Radiation Dose (MRad) | Relative Viscosity 0.1 rad/s (Pa-s) | Relative Viscosity 100 rad/s (Pa-s) |
|---|---|---|---|
| Neat mPP | 2.5 | 0.047 | 0.037 |
|  | 5 | 0.016 | 0.009 |
|  | 10 | 0.013 | 0.008 |
| mPP + 5 wt % PIB-A | 2.5 | 0.158 | 0.266 |
|  | 5 | 0.043 | 0.060 |
|  | 10 | 0.016 | 0.020 |
| mPP + 10 wt % PIB-A | 2.5 | 0.156 | 0.237 |
|  | 5 | 0.042 | 0.066 |
|  | 10 | 0.018 | 0.022 |
| mPP + 5 wt % PIB-B | 2.5 | 0.105 | 0.150 |
|  | 5 | 0.025 | 0.018 |
|  | 10 | 0.016 | 0.015 |
| mPP + 10 wt % PIB-B | 2.5 | 0.089 | 0.149 |
|  | 5 | 0.020 | 0.014 |
|  | 10 | 0.015 | 0.013 |

While the present invention has been described and illustrated by reference to particular embodiments, those of ordinary skill in the art will appreciate that the invention lends itself to many different variations not illustrated herein. For these reasons, then, reference should be made solely to the appended claims for purposes of determining the scope of the present invention. Further, certain features of the present invention are described in terms of a set of numerical upper limits and a set of numerical lower limits. It should be appreciated that ranges formed by any combination of these limits are within the scope of the invention unless otherwise indicated.

All priority documents are herein fully incorporated by reference for all jurisdictions in which such incorporation is permitted. Further, all documents cited herein, including testing procedures, are herein fully incorporated by reference for all jurisdictions in which such incorporation is permitted.

We claim:

1. A sterilized article comprising a plasticized polyolefin composition comprising one or more polyolefins and one of more non-functionalized plasticizers where the non-functionalized plasticizer comprises $C_6$ to $C_{1500}$ paraffins having a kinematic viscosity of 10 cSt or more at 100° C., a specific gravity of 0.700 to 0.860 and a viscosity index of 120 or more, wherein elastomers are substantially absent from the composition, and ethylene homopolymers and ethylene copolymers having a weight average molecular weight of from 500 to 10,000, are not added deliberately to the plasticized polyolefin composition and if said ethylene homopolymers and copolymers are present, said ethylene homopolymers and copolymers are present at less than 1 weight %, and wherein the article has been subjected to an amount of radiation sufficient to sterilize the article.

2. The sterilized article of claim 1, wherein the non-functionalized plasticizer comprises oligomers of $C_5$ to $C_{14}$ olefins.

3. The sterilized article of claim 1, wherein the non-functionalized plasticizer has a pour point of −5° C. or less.

4. The sterilized article of claim 1, wherein the non-functionalized plasticizer comprises oligomers of $C_8$ to $C_{12}$ olefins.

5. The sterilized article of claim 1, wherein the non-functionalized plasticizer comprises oligomers of two or more different olefins.

6. The sterilized article of claim 1 wherein the non-functionalized plasticizer comprises oligomers of $C_8$, $C_{10}$ and $C_{12}$ olefins.

7. The sterilized article of claim 1, wherein the non-functionalized plasticizer has an $M_n$ of 500 to 10,000.

8. The sterilized article of claim 1, wherein the non-functionalized plasticizer comprises an oligomer of decene having a carbon number of 40-200.

9. The sterilized article of claim 1, wherein the non-functionalized plasticizer comprises a mineral oil having a saturates levels of 90% or more, and sulfur content of 0.03% or less.

10. The sterilized article of claim 1, wherein the non-functionalized plasticizer comprises a mineral oil having a saturates levels of 98% or more, and sulfur content of 0.01% or less.

11. The sterilized article of claim 1, wherein the non-functionalized plasticizer has a viscosity index of 130 or more.

12. The sterilized article of claim 1, wherein the non-functionalized plasticizer comprises a linear or branched paraffinic hydrocarbon composition having a number average molecular weight of 500 to 20,000, having less than 10% sidechains having 4 or more carbons, and having at least 1 or 2 carbon branches present at 15 weight % or more, and where the non-functionalized plasticizer comprises less than 2 weight % cyclic paraffins.

13. The sterilized article of claim 1, wherein the non-functionalized plasticizer is present at 0.01 to 60 weight %, based upon the weight of the polyolefin and the non-functionalized plasticizer.

14. The sterilized article of claim 1, wherein the non-functionalized plasticizer is present at 3 to 50 weight %, based upon the weight of the polyolefin and the non-functionalized plasticizer.

15. The sterilized article of claim 1, wherein the non-functionalized plasticizer is present at 5 to 20 weight %, based upon the weight of the polyolefin and the non-functionalized plasticizer.

16. The sterilized article of claim 1, wherein the polyolefin comprises polypropylene.

17. The sterilized article of claim 1, wherein the polyolefin comprises a random copolymer comprising propylene and at least one other alpha-olefin.

18. The sterilized article of claim 1, wherein the polyolefin comprises a random copolymer comprising propylene and at least one other alpha-olefin selected from the group consisting of ethylene, butene, hexene, and octene.

19. The sterilized article of claim 1, wherein the polyolefin comprises homopolypropylene.

20. The sterilized article of claim 1, wherein the polyolefin comprises polypropylene having a weight average molecular weight of from 10,000 to 400,000 and a molecular weight distribution of from 1 to 9.

21. The sterilized article of claim 1, wherein the polyolefin comprises polypropylene having a weight average molecular weight of from 40,000 to 300,000 and a molecular weight distribution of from 1 to 6.

22. The sterilized article of claim 1, wherein the polyolefin comprises polypropylene having a weight average molecular weight of from 50,000 to 200,000 and a molecular weight distribution of from 1 to 4.

23. The sterilized article of claim 1, wherein the article further comprises from 0.01 to about 0.5 wt % hindered amine stabilizer.

24. The sterilized article of claim 1, wherein the article further comprises up to 1 wt % of a thiopropionate antioxidant and/or up to 0.5 wt % of a phosphite antioxidant and/or up to 0.5 wt % clarifying nucleator.

25. The sterilized article of claim 1, wherein the non-functionalized plasticizer has a kinematic viscosity of 50 cSt or more at 100° C.

26. The sterilized article of claim 1, wherein the non-functionalized plasticizer has an $M_n$ of 500 to 21,000.

27. The sterilized article of claim 1, wherein the non-functionalized plasticizer has a dielectric constant at 20° C. of less than 3.0.

28. The sterilized article of claim 1, wherein the non-functionalized plasticizer has a specific gravity of 0.700 to 0.850.

29. The sterilized article of claim 1, wherein said article is a film.

30. The sterilized article of claim 1, wherein said article is packaging material.

31. The sterilized article of claim 1, wherein said article is packaging material which is a self supporting multilayered structure.

32. The sterilized article of claim 1, wherein said article is packaging material which is a self supporting multilayered structure comprising plastic film.

33. The sterilized article of claim 1, wherein said article is packaging material which is a self supporting multilayered structure comprising metal foil.

34. The sterilized article of claim 1, wherein said article is packaging material which is a self supporting multilayered structure comprising cellulosic material.

35. The sterilized article of claim 1, wherein said article is selected from the group consisting of unit-dose packs, blister packs, bubble packs, wrapping material, and containers for food preserved by irradiation.

36. The sterilized article of claim 1, where the polyolefin is polypropylene and wherein said article is formed by a process selected from the group consisting of extrusion, blowing, blow-molding, and lamination, and wherein the increased radiation tolerance of the article is evidenced by at least 20% greater Gardner impact strength after treatment with up to 10 MRads of gamma or beta radiation than would be found for the same article made from the polypropylene alone which has been subjected to the same radiation dose.

37. The sterilized article of claim 1, where the polyolefin is polypropylene and wherein said article is formed by a process selected from the group consisting of extrusion, blowing, blow-molding, and lamination, and wherein increased radiation tolerance of the article is evidenced by a Gardner impact strength after treatment with up to 10 MRads of gamma or beta radiation that is at least 2000 greater for each percent of non-functionalized plasticizer than would be found for the same article made from the polypropylene alone which has been subjected to the same radiation dose.

38. The sterilized article of claim 1, wherein said article is a medical device.

39. The sterilized article of claim 1, wherein the article is a medical device formed by a process selected from the group consisting of extrusion, blowing, lamination, blow molding, transfer molding, injection molding, pultrusion, protrusion, draw reduction, rotational molding, spinbonding, melt spinning, and melt blowing.

40. The sterilized article of claim 1, wherein the article is a syringe or component of a syringe.

41. The sterilized article of claim 1, wherein said article has been subjected to radiation in an amount of 0.5 to 10 MRad.

42. The sterilized article of claim 1 wherein the plasticized polyolefin composition comprises a nucleating agent.

43. The sterilized article of claim 42 wherein the nucleating agent is selected from the group consisting of sodium benzoate, sodium 2,2'-methylenebis(4,6-di-tert-butylphenyl) phosphate, aluminum 2,2'-methylenebis(4,6-di-tert-butylphenyl) phosphate, dibenzylidene sorbitol, di(p-tolylidene) sorbitol, di(p-ethylbenzylidene) sorbitol, bis(3,4-dimethylbenzylidene) sorbitol, and N',N'-dicyclohexyl-2,6-naphthalenedicarboxamide, bis-4-methylbenzylidene sorbitol, bis-3,4,-dimethylbenzylidene sorbitol and salts of disproportionated rosin esters.

44. The sterilized article of claim 42 wherein the nucleating agent is comprises bis-4-methylbenzylidene sorbitol or bis-3,4,-dimethylbenzylidene sorbitol.

45. The sterilized article of claim 1 wherein the plasticizer has a specific gravity of 0.700 to 0.855.

46. The sterilized article of claim 1 where the polyolefin comprises an impact copolymer that is a reactor blend.

47. The sterilized article of claim 1 where the plasticized polyolefin composition further comprises a plastomer.

48. The sterilized article of claim 1 where the polyolefin is a polypropylene having a melting point (second melt) of 30 to 185° C.

49. The sterilized article of claim 1 where the polyolefin is a polypropylene having a crystallinity of 10 to 70%.

50. The sterilized article of claim 1 where the polyolefin is a polypropylene having a heat of fusion between 20 to 150 J/g.

51. The sterilized article of claim 1 where the polyolefin is a polypropylene having a Gardner impact strength, tested on 0.125 inch disk at 23° C., of 20 in-lb to 1000 in-lb.

52. The sterilized article of claim 1 where the polyolefin is polypropylene having a 100 secant flexural modulus of from 100 MPa to 2300 MPa.

53. The sterilized article of claim 1 where the polyolefin comprises a copolymer of propylene and from 0.5 to 30 weight % of one or more comonomers selected from the group consisting of ethylene, butene, pentene, hexene, heptene, octene, nonene, decene, dodecene, 4-methyl-pentene-1, 3-methyl pentene-1,5-ethyl-1-nonene, and 3,5,5-trimethyl-hexene-1.

54. The sterilized article of claim 1 wherein the polyolefin is an in situ propylene impact copolymer having a 10% secant flexural modulus of from 300 MPa to 2300 MPa and comprising from 40% to 95% by weight of a Component A and from 5% to 60% by weight of a Component B based on the total weight of copolymer; wherein Component A comprises propylene homopolymer or copolymer, the copolymer comprising boo or less by weight ethylene, butene, hexene or octene comonomer; and wherein Component B comprises propylene copolymer, wherein the copolymer comprises from 5% to 70% by weight ethylene, butene, hexene and/or octene comonomer, and from 95% to 30% by weight propylene.

55. The sterilized article of claim 54 wherein the refractive index of Component A and the refractive index of Component B are within 10% of each other, and, optionally the refractive index of the non-functionalized plasticizer is within 20% of Component A, Component B or both.

56. The sterilized article of claim 54 wherein the plastomer has a 10% secant flexural modulus of from 10 MPa to 150 MPa.

57. The sterilized article of claim 47 where the plastomer is a copolymer of ethylene and from 2 to 35 weight % of $C_3$ to $C_{10}$ alpha-olefin derived units.

58. The sterilized article of claim 47 wherein the plastomer has a melting temperature of from 30 to 80° C. (first melt peak) and from 50 to 125 (second melt peak).

59. The sterilized article of claim 47 wherein the plastomer comprises a metallocene catalyzed copolymer of ethylene and propylene, 1-butene, 1-hexene, or 1-octene having a density of 0.86 to 0.900 g/cm$^3$ and an Mw/Mn of 1.5 to 5.

60. The sterilized article of claim 1 where the polyolefin is a propylene homopolymer or copolymer having an Mw of from 50,000 to 2,000,000 g/mol.

61. The sterilized article of claim 1 where the plasticized polyolefin composition excludes physical blends of polypropylene with other polyolefins.

62. A sterilized article comprising a plasticized polypropylene composition comprising polypropylene and one of more non-functionalized plasticizers where the non-functionalized plasticizer comprises $C_6$ to $C_{1500}$ paraffins having a kinematic viscosity of 10 cSt or more at 100° C., a specific gravity of 0.700 to 0.860 and a viscosity index of 120 or more, wherein elastomers are substantially absent from the composition, and where ethylene homopolymers and copolymers having a weight average molecular weight of from 500 to 10,000, are not added deliberately to the plasticized polypropylene composition and if said ethylene homopolymers and copolymers are present, said ethylene homopolymers and copolymers are present at less than 1 weight %, wherein the article is formed by a process selected from the group consisting of extrusion, blowing, blow-molding, and lamination and the article has been subjected to an amount of radiation sufficient to sterilize the article, wherein the increased radiation tolerance of the article is evidenced by at least 20% greater Gardner impact strength after treatment with up to 10 MRads of gamma or beta radiation than would be found for the same article made from the polypropylene alone which has been subjected to the same radiation dose.

63. The sterilized article of claim 1 where the polyolefin is a propylene homopolymer or copolymer having an Mw of from 50,000 to 2,000,000 g/mol and having a 100 Secant flexural modulus of 200 to 2300 MPa.

64. A sterilized nonwoven article comprising a plasticized polyolefin composition comprising one or more polyolefins and one of more non-functionalized plasticizers where the non-functionalized plasticizer comprises $C_6$ to $C_{1500}$ paraffins having a kinematic viscosity of 10 cSt or more at 100° C., a specific gravity of 0.700 to 0.860, and a viscosity index of 120 or more, wherein elastomers are substantially absent from the composition and where ethylene homopolymers and copolymers having a weight average molecular weight of from 500 to 10,000 are substantially absent, and wherein the article has been subjected to an amount of radiation sufficient to sterilize the article.

* * * * *

UNITED STATES PATENT AND TRADEMARK OFFICE
CERTIFICATE OF CORRECTION

PATENT NO. : 7,622,523 B2 Page 1 of 1
APPLICATION NO. : 11/054247
DATED : November 24, 2009
INVENTOR(S) : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 255 days.

Signed and Sealed this

Twenty-sixth Day of October, 2010

David J. Kappos
*Director of the United States Patent and Trademark Office*